US011648383B2

(12) United States Patent
Hallisey et al.

(10) Patent No.: US 11,648,383 B2
(45) Date of Patent: May 16, 2023

(54) MEDICAL BREAK-AWAY CONNECTORS

(71) Applicant: Merit Medical Systems, Inc., South Jordan, UT (US)

(72) Inventors: Denise Hallisey, Wethersfield, CT (US); Jim Mottola, West Jordan, UT (US); Brian Stevens, Pleasant Grove, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 378 days.

(21) Appl. No.: 16/799,497

(22) Filed: Feb. 24, 2020

(65) Prior Publication Data

US 2020/0261710 A1    Aug. 20, 2020

Related U.S. Application Data

(63) Continuation of application No. 15/228,796, filed on Aug. 4, 2016, now Pat. No. 10,569,073.

(60) Provisional application No. 62/249,713, filed on Nov. 2, 2015, provisional application No. 62/202,377, filed on Aug. 7, 2015.

(51) Int. Cl.
*A61M 39/10* (2006.01)
*A61M 39/26* (2006.01)

(52) U.S. Cl.
CPC ........ *A61M 39/10* (2013.01); *A61M 39/1011* (2013.01); *A61M 39/26* (2013.01); *A61M 2039/1033* (2013.01); *A61M 2039/1061* (2013.01)

(58) Field of Classification Search
CPC .......... A61M 2039/1033; A61M 39/10; A61M 2039/1027; A61M 39/1055; A61M 2039/1061; A61M 2039/1077; A61M 2039/1083; A61M 2039/1088; A61M 39/1011; A61M 39/26
See application file for complete search history.

(56) References Cited

U.S. PATENT DOCUMENTS 1,303,367 A  *  5/1919  Nelson ................. F16L 37/252
                                                        285/70
2,204,392 A  *  6/1940  Arm .................... F16L 37/248
                                                        285/379

(Continued)

FOREIGN PATENT DOCUMENTS

WO    2003090843    11/2003
WO    2005004974    1/2005

(Continued)

OTHER PUBLICATIONS

European Search Report dated Jan. 31, 2019 for EP16835668.1.

(Continued)

*Primary Examiner* — Quynh-Nhu H. Vu
(74) *Attorney, Agent, or Firm* — Dorsey & Whitney LLP

(57) ABSTRACT

Break-away connectors are disclosed. The break-away connectors may be configured to be coupled in at least two configurations, for example, a high force configuration and a low force configuration. The break-away connectors may also be incrementally adjustable between the high force configuration and the low force configuration. The break-away connectors may be coupled to a first medical device and a second medical device. Methods of using and/or coupling the break-away connectors are also disclosed.

11 Claims, 18 Drawing Sheets

(56) References Cited

U.S. PATENT DOCUMENTS

| | | | |
|---|---|---|---|
| 2,933,333 A * | 4/1960 | Bredtschneider | F16L 29/005 285/119 |
| 3,751,077 A * | 8/1973 | Hiszpanski | F16L 19/0225 285/332 |
| 3,844,585 A * | 10/1974 | Sands | F16L 29/005 285/3 |
| 4,142,769 A | 3/1979 | Wood | |
| 4,441,775 A | 4/1984 | Walters | |
| 4,451,069 A * | 5/1984 | Melone | F16L 37/0842 285/86 |
| 4,826,486 A | 5/1989 | Palsrok | |
| 4,895,570 A * | 1/1990 | Larkin | A61M 39/1011 604/905 |
| 5,405,336 A | 4/1995 | Austin et al. | |
| 5,492,147 A | 2/1996 | Challender et al. | |
| 5,509,911 A * | 4/1996 | Cottone, Sr. | A61M 39/1055 604/905 |
| 5,636,875 A | 6/1997 | Wasser et al. | |
| 5,651,776 A * | 7/1997 | Appling | A61M 39/10 285/332 |
| 5,816,835 A * | 10/1998 | Meszaros | H01R 13/53 439/205 |
| 6,168,137 B1 * | 1/2001 | Paradis | A61M 39/26 251/149.6 |
| 6,402,723 B1 * | 6/2002 | Lampropoulos | A61M 39/0613 604/256 |
| 6,641,574 B2 | 11/2003 | Badia Segura et al. | |
| 6,776,638 B2 | 8/2004 | Thurston | |
| 7,004,934 B2 | 2/2006 | Vaillancourt | |
| 7,303,553 B2 | 12/2007 | Ott | |
| 7,766,394 B2 | 8/2010 | Sage et al. | |
| D636,079 S | 4/2011 | Leypold | |
| 8,235,971 B2 | 8/2012 | Christensen et al. | |
| 8,790,327 B2 | 7/2014 | Takemoto | |
| D750,236 S | 2/2016 | Maurice | |
| D757,260 S | 5/2016 | Lombardi, III | |
| D773,659 S | 12/2016 | Cain | |
| D784,529 S | 4/2017 | Steele | |
| D792,586 S | 7/2017 | Becker | |
| D799,032 S | 10/2017 | Becker | |
| D825,746 S | 8/2018 | Davis | |
| D830,523 S | 10/2018 | Vranish | |
| D830,524 S | 10/2018 | Vranish | |
| D836,191 S | 12/2018 | Kheradpir | |
| D837,978 S | 1/2019 | Pappalardo | |
| 2003/0098430 A1 | 5/2003 | Leinsing | |
| 2005/0015075 A1 | 1/2005 | Wright et al. | |
| 2005/0251102 A1 | 11/2005 | Hegland et al. | |
| 2010/0030163 A1 | 2/2010 | Carrez et al. | |
| 2010/0219630 A1 | 9/2010 | Readman | |
| 2011/0009849 A1 | 1/2011 | Christensen et al. | |
| 2011/0015581 A1 | 1/2011 | Fangrow, Jr. | |
| 2013/0030387 A1 | 1/2013 | Williams et al. | |
| 2014/0209197 A1 * | 7/2014 | Carrez | F16L 37/38 137/798 |
| 2014/0284917 A1 * | 9/2014 | Tiberghien | F16L 19/0225 285/87 |
| 2014/0358120 A1 | 12/2014 | Haarala | |
| 2015/0032089 A1 | 1/2015 | Way | |
| 2015/0157849 A1 | 6/2015 | Phillips et al. | |
| 2016/0199634 A1 | 7/2016 | Gagliardoni | |
| 2020/0261710 A1 | 8/2020 | Hallisey et al. | |

FOREIGN PATENT DOCUMENTS

| | | |
|---|---|---|
| WO | 2006010929 | 2/2006 |
| WO | 2012088463 | 6/2012 |

OTHER PUBLICATIONS

European Search Report dated Feb. 12, 2019 for EP16835668.1.
International Search Report and Written Opinion dated Dec. 5, 2016 for PCT/US2016/045601.
Notice of Allowance dated Jul. 31, 2019 for U.S. Appl. No. 29/642,644.
Notice of Allowance dated Nov. 7, 2019 for U.S. Appl. No. 15/228,796.
Office Action dated Jan. 28, 2019 for U.S. Appl. No. 15/228,796.
Office Action dated Mar. 10, 2010 for U.S. Appl. No. 29/642,655.
Office Action dated Apr. 2, 2019 for U.S. Appl. No. 29/642,644.
Office Action dated Jun. 25, 2019 for U.S. Appl. No. 15/228,796.
Office Action dated Aug. 2, 2018 for U.S. Appl. No. 15/228,796.
Mottola, et al., U.S. Appl. No. 29/642,655, filed Mar. 30, 2018.
Notice of Allowance dated Oct. 15, 2020 for U.S. Appl. No. 29/642,655.

* cited by examiner

MEDICAL BREAK-AWAY CONNECTORS

RELATED APPLICATIONS

This application is a continuation of U.S. patent application Ser. No. 15/228,796, filed on Aug. 4, 2016, and titled, "Medical Break-Away Connectors," which claims priority to U.S. Provisional Application No. 62/249,713 filed on Nov. 2, 2015 and titled, "Medical Break-Away Connectors," and U.S. Provisional Application No. 62/202,377 filed on Aug. 7, 2015 and titled, "Medical Break-Away Connectors," all of which are hereby incorporated by reference in their entireties.

TECHNICAL FIELD

The present disclosure relates generally to medical break-away connectors. More specifically, the present disclosure relates to break-away connectors configured to be coupled in at least two different configurations and methods of coupling the break-away connectors.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

DETAILED DESCRIPTION

Figure 1A:
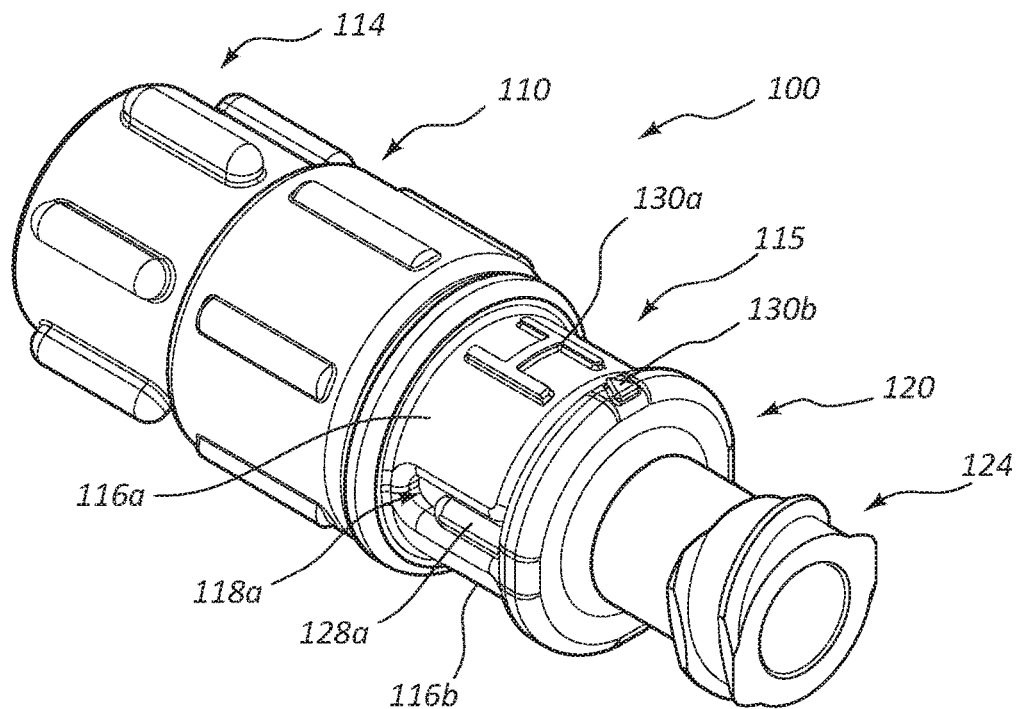
FIG. 1A is a perspective view of a break-away connector in a coupled state.

The various embodiments disclosed herein generally relate to medical break-away connectors. In some embodiments, the break-away connectors comprise a valve, while in some other embodiments, the break-away connectors do not comprise a valve. Break-away connectors may comprise a first body member and a second body member, wherein the first and second body members are configured to be coupled to one another in at least two configurations or settings. Also disclosed herein are methods of coupling break-away connectors.

Various features of the connectors disclosed herein may be grouped together in a single embodiment, figure, or description thereof for the purpose of streamlining the disclosure. Many of these features may be used alone and/or in combination with one another in the various embodiments.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. In some instances, break-away connectors may be used as part of a line of medical tubing extending from a patient. As used herein, opposite ends of the breakaway connectors are defined with reference to use in a line of medical tubing extending from the patient. As such, the proximal end of a break-away connector refers to the end oriented away from the patient (along the line of tubing) and the distal end the opposite, or the end closest to the patient along the line of medical tubing. This coordinate system is utilized regardless of whether the connector is coupled to a patient or line of tubing. Notwithstanding this coordinate system, it is within the scope of this disclosure to reverse the orientation (along a line of medical tubing coupled to a patient) of the connectors disclosed herein, in some instances.

The term "resilient" refers to a component, device, or object having a particular shape that can then be elastically deformed into a different shape, but that may return to the original shape when unconstrained. For example, a resilient arm may extend along the longitudinal direction of a connector and, in use, the resilient arm may then be constrained (i.e., temporarily engaged with and/or disposed over a ridge portion) to elastically deform it into a second shape (i.e., displaced radially outward due to interaction with the ridge), then unconstrained (i.e., removed from engagement with the ridge portion) such that the resilient arm returns to its first shape or substantially returns to its first shape.

The present disclosure generally relates to medical break-away connectors. In some embodiments, the break-away connector may comprise a first body member configured to be coupled to a second body member such that fluid communication is provided between each of the first body member and the second body member. The first body member may be coupleable to the second body member, or vice versa, in at least two configurations or settings. In various embodiments, a greater force may be utilized or needed (i.e., as applied or exerted by a practitioner or by a patient) to uncouple the first body member from the second body member when the break-away connector is in a first configuration or first setting in comparison to when the break-away connector is in a second configuration or second setting. Furthermore, a transition between the first configuration and the second configuration, and vice versa, may be substantially limited, minimized, or prevented when the first body member is coupled to the second body member. A degree or level of strength or tightness of the coupling of the first body member to the second body member may also be continuously or incrementally adjustable between each of the first configuration and the second configuration, and vice versa.

A fluid seal or valve limiting flow through the body members of a break-away connector may be associated with one or both of the first and second body members. For example, in some embodiments, the first body member may comprise a valve such that fluid communication through at least a portion of the first body member is substantially limited or minimized when the first body member is uncoupled from the second body member. Likewise, the second body member may comprise a valve such that fluid communication through at least a portion of the second body member is substantially limited or minimized when the second body member is uncoupled from the first body member. In some instances, coupling of the body members may be configured to open the valve.

In some embodiments, a break-away connector of the present disclosure may be configured to be placed in fluid communication with a volume of a fluid. Additionally, the break-away connector may be configured such that the break-away connector may be coupled to one or more of a catheter, an access device, tubing, or another suitable apparatus. For example, a proximal end of the break-away connector may be coupled to a tube, while a distal end of the break-away connector may be coupled to a catheter, or vice versa. In certain embodiments, the break-away connector may be configured to allow or permit the flow or passage of a fluid into and/or out of a patient. For example, the break-away connector, when coupled to a catheter or tubing, may be used in an intravenous feeding of a patient or in a drainage of a volume of a fluid from a patient.

In various embodiments, a catheter may be disposed within a patient at an access site. A proximal end of the catheter that is exterior of the patient may be coupled to a distal end of a break-away connector. Furthermore, a distal end of a tube that is also exterior to the patient may be coupled to a proximal end of the break-away connector and a proximal end of the tube may be coupled to a volume of a fluid, such as a collection bag (i.e., for a drainage catheter). In some embodiments, if the patient is ambulatory, the one or more catheters, tubes, and/or break-away connector may catch on to or interact with an object such as a chair or a door knob. Such catching or interaction may pull on or otherwise disturb at least a portion of the catheter. Furthermore, such catching or interaction may cause or result in damage or injury to the access site of the patient. Such catching or interaction may also result in the catheter being displaced or pulled out of the patient. In some embodiments, a break-away connector as described herein may limit or minimize displacement of the catheter out of a patient and/or limit or minimize injury to the access site of the patient. For example, the break-away connector may be configured such that it uncouples (i.e., into a separate first body member and a separate second body member) when a force above a predetermined level is applied to the break-away connector or to one or more devices coupled to the break-away connector.

In various embodiments, the break-away connector may be configured such that the break-away connector is relatively easy to uncouple and in various other embodiments the break-away connector may be configured such that the break-away connector is relatively difficult to uncouple. The selected strength or tightness of the coupling may depend, at least in part, on the condition or sensitivity of the access site and/or the patient. The break-away connector may also be configured such that leakage of a fluid that is flowing or passing through the break-away catheter and/or tubing is limited or minimized upon uncoupling of the break-away connector. For example, the break-away connector may comprise one or more valves that are configured to inhibit, limit, or minimize fluid flow through the first body member and/or the second body member of the break-away connector when the break-away connector is in an uncoupled state.

Figure 1B:
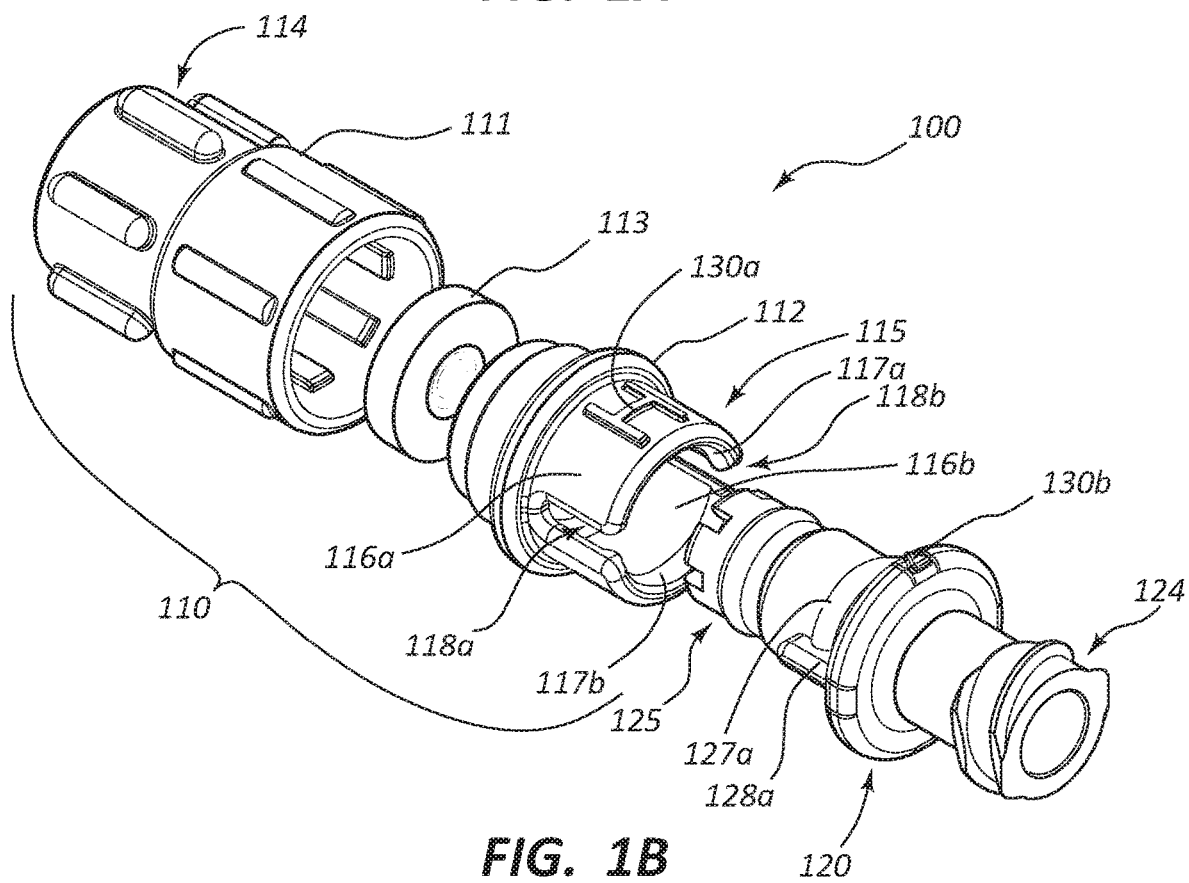
FIG. 1B is an exploded view of the break-away connector of FIG. 1A.

FIG. 1A is a perspective view of a break-away connector 100 in a coupled state, and FIG. 1B is an exploded view of the break-away connector 100 of FIG. 1A. As illustrated, the break-away connector 100 can comprise a first body member 110 and a second body member 120. In the exploded view of FIG. 1B, individual components of the first body member 110 are shown in an unassembled state. The uncoupled state of the break-away connector 100 corresponds to a configuration wherein the components of the first body member 110 are assembled together, but the first body member 110 and the second body member 120 are not coupled. The components of the first body member 110 may be assembled and coupled during manufacture, while the first body member 110 and the second body member 120 may be selectively coupleable by a user.

Again, in some embodiments, the first body member 110 can be coupled to the second body member 120, and vice versa, by a user. With reference to FIG. 1B, the first body member 110 may comprise a first portion 111, a second portion 112, and a valve 113. The valve 113 may be disposed within the first body member 110 (i.e., between each of the first portion 111 and the second portion 112). The first portion 111 and the second portion 112 may be coupled to each other by at least one of a compression fit, a snap fit, an adhesive, or another suitable coupling mechanism. In some embodiments, the first body member may comprise only a single portion or another suitable number of portions.

The first body member 110 can further comprise a coupling end portion 114 and a break-away end portion 115. As depicted, the coupling end portion 114 may be disposed at an end of the first body member 110 opposite from the break-away end portion 115. The coupling end portion 114, as illustrated, comprises a male connector. As discussed in further detail below, however, the coupling end portion 114 may comprise any suitable coupling mechanism. The first body member 110 may further comprise one or more resilient arms. For example, the first body member 110 may comprise a first resilient arm 116a and a second resilient arm 116b, wherein the resilient arms 116a, 116b extend longitudinally away from the coupling end portion 114 of the first body member 110. Furthermore, the one or more resilient arms 116a, 116b may comprise one or more ridge portions or raised portions. For example, the first resilient arm 116a may comprise a first ridge portion 117a extending inwardly toward a longitudinal axis of the break-away connector 100, and the second resilient arm 116b may comprise a second ridge portion 117b extending inwardly toward the longitudinal axis of the break-away connector 100. One or more slots may be disposed adjacent, between, or within the one or more resilient arms 116a, 116b. For example, as illustrated, a first slot 118a and a second slot 118b can be disposed between each of the first resilient arm 116a and the second resilient arm 116b. In some embodiments, the break-away connector 100 may comprise one, two, three, four, five, or more resilient arms, ridge portions, and/or slots.

Likewise, the second body member 120 can also comprise a coupling end portion 124 and a break-away end portion 125, wherein the coupling end portion 124 may be disposed at an end of the second body member 120 opposite from the break-away end portion 125. The coupling end portion 124, as illustrated, comprises a female connector. Again, as discussed in further detail below, the coupling end portion 124 may also comprise any suitable coupling mechanism. The break-away end portion 125 of the second body member 120 can comprise one or more ridge portions or raised portions. For example, the break-away end portion 125 can comprise a first ridge portion 127a and a second ridge portion 127b (see FIG. 1C). One or more ribs may also be disposed adjacent or between the one or more ridge portions 127a, 127b. For example, the break-away end portion 125 may comprise a first rib 128a and a second rib, wherein the second rib is disposed on a portion of the second body member 120 that is opposite of the portion of the break-away end portion 125 comprising the first rib 128a. In certain embodiments, the one or more ribs 128a may be configured to be at least partially disposed within at least a portion of the one or more slots 118a, 118b upon coupling of the first and second body members 110, 120.

In various embodiments, the one or more ridge portions 117a, 117b of the first body member 110 may be configured to engage or interact with the one or more ridge portions 127a, 127b of the second body member 120. Additionally, the first and second body members 110, 120 may be coupleable in at least two configurations or settings. In some embodiments, a greater force may be required to uncouple the first body member 110 from the second body member 120 when the break-away connector 100 is in a first configuration or a first setting in comparison to when the break-away connector 100 is in a second configuration or a second setting. For example, a practitioner uncoupling the first body member 110 from the second body member 120 may apply, exert, or utilize a greater amount of force (i.e., mechanical force) to uncouple the first body member 110 from the second body member 120 when the break-away connector 100 is in the first configuration than when the break-away connector 100 is in the second configuration. In some other embodiments, the first and second body members 110, 120 may be coupleable in three, four, five, or more configurations, wherein each configuration may comprise a different level of strength or tightness.

In some embodiments, an amount of force needed to uncouple the first body member 110 from the second body member 120 may be less than an amount of force needed to dislodge a suture, or to remove a catheter from a patient. For example, the amount of force needed to uncouple the first body member 110 from the second body member 120, and vice versa, may be less than at least 10 pounds, less than at least 5 pounds, less than at least 4 pounds, less than at least 2 pounds, etc. In various embodiments, the amount of force needed to uncouple the first body member 110 from the second body member 120 may be between about 0.5 pounds and about 10 pounds, between about 0.5 pounds and about 8 pounds, between about 0.5 pounds and about 6 pounds, between about 0.5 pounds and about 5 pounds, between about 0.5 pounds and about 4 pounds, between about 0.5 pounds and about 2 pounds, and so on. In some embodiments, the amount of force needed to uncouple the first body member 110 from the second body member 120 may be between about 0.5 pounds and about 10 pounds, between about 2 pounds and about 10 pounds, between about 4 pounds and about 10 pounds, between about 5 pounds and about 10 pounds, between about 8 pounds and about 10 pounds, between about 9.5 pounds and about 10 pounds, and so on. In certain embodiments, the amount of force needed to uncouple the first body member 110 from the second body member 120 may be between about 0.5 pounds and about 10 pounds, between about 2 pounds and about 4 pounds, between about 2 pounds and about 8 pounds, between about 4 pounds and about 8 pounds, between about 6 pounds and about 8 pounds, between about 4 pounds and about 6 pounds, and so on. Such amounts of force needed to uncouple a first body member from a second body member of a break-away connector may analogously and/or equally apply to all embodiments of the break-away connector as described herein (e.g., break-away connectors 100, 200, 300, 400, 500, 600).

Figure 1C:
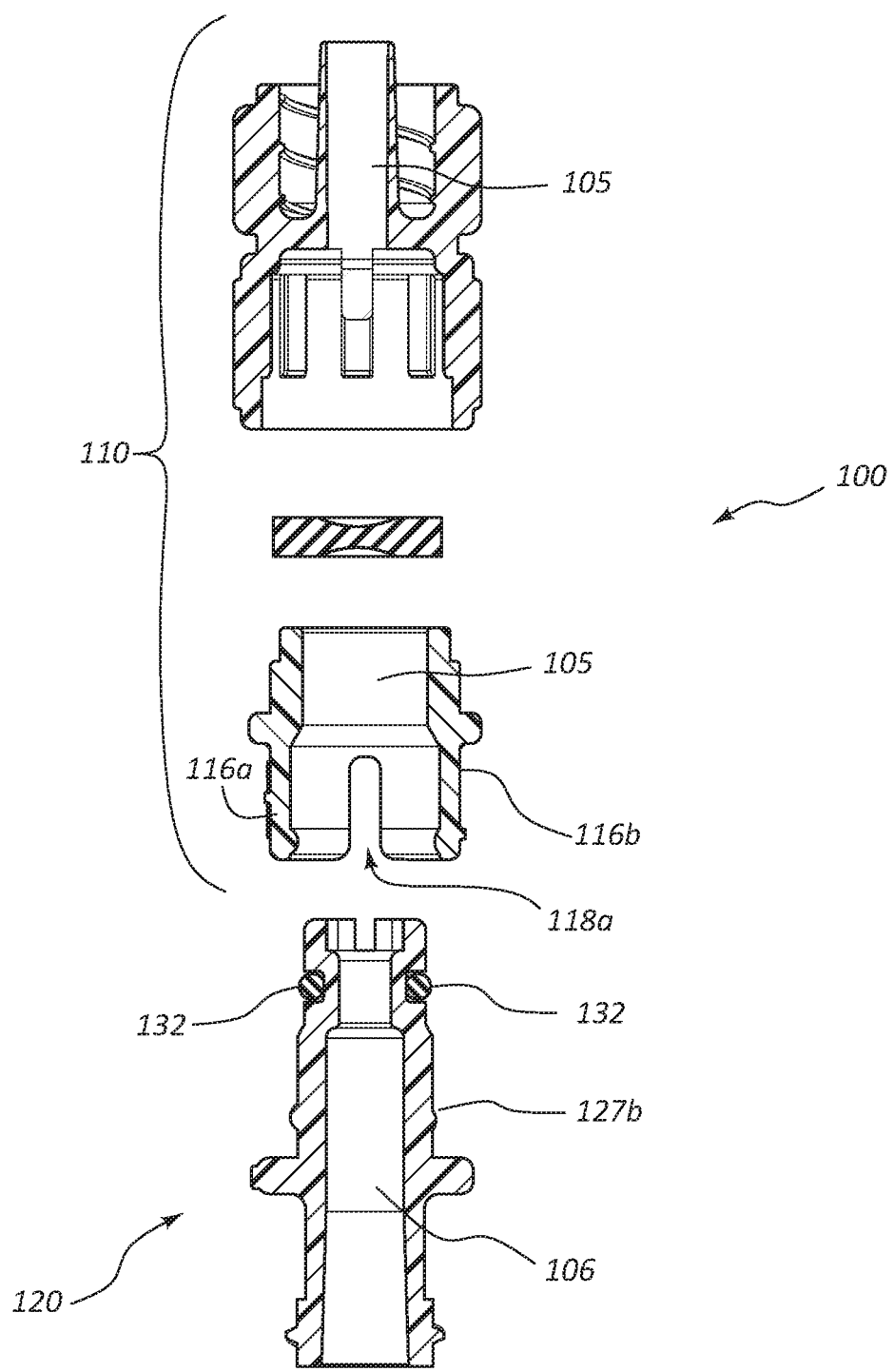
FIG. 1C is an exploded cross-sectional side view of the break-away connector of FIG. 1A.

FIG. 1C is an exploded cross-sectional side view of the break-away connector 100 of FIG. 1A. As depicted, the first body member 110 can comprise two resilient arms 116a, 116b. Additionally, the slot 118a can be at least partially disposed between each of the two resilient arms 116a, 116b. As discussed above, the second body member 120 can comprise one or more ribs 128a (see FIGS. 1A and 1B). In certain embodiments, at least a portion of the one or more ribs 128a can be configured to be disposed within at least a portion of the one or more slots 118a, 118b when the first body member 110 is coupled to the second body member 120, such that rotation of the first body member 110 in relation to the second body member 120 around a longitudinal axis of the break-away connector 100 may be substantially limited or minimized. Stated another way, the engagement or interaction of the first body member 110 with the second body member 120, via the slots, resilient arms, and ribs, may substantially limit or minimize displacement or rotation of the first body member 110 and the second body member 120 between each of the first configuration and the second configuration, and vice versa. Still further, interaction of the one or more ribs 128a (see FIGS. 1A and 1B) and a portion of the one or more slots 118a, 118b may facilitate alignment of the first body member 110 and the second body member 120 when coupled.

In some other embodiments, the first body member 110 may comprise only one resilient arm, wherein the one resilient arm may comprise a single slot. Furthermore, the second body member 120 may comprise only one rib, wherein at least a portion of the rib is configured to be disposed within at least a portion of the slot when the first and second body members 110, 120 are coupled to each other, such that rotation of the first body member 110 in relation to the second body member 120 around the longitudinal axis of the break-away connector 100 is substantially limited or minimized. As discussed above, engagement or interaction of the rib with the slot may substantially limit or minimize rotation of the first body member 110 in relation to the second body member 120, or vice versa.

As shown in FIG. 1C, the first body member 110 can further comprise a first lumen 105 disposed within at least a portion of the first body member 110, wherein the first lumen 105 is configured to provide fluid communication between a first end and a second end of the first body member 110. The second body member 120 can also further comprise a second lumen 106 disposed within at least a portion of the second body member 120, wherein the second lumen 106 is configured to provide fluid communication between a first end and a second end of the second body member 120. Furthermore, when the first and second body members 110, 120 are coupled to one another, the first lumen 105 may be configured to be in fluid communication with the second lumen 106 (i.e., the first lumen 105 may be substantially aligned with the second lumen 106).

The break-away connector 100, as illustrated, may further comprise a seal member 132, wherein the seal member 132 is configured to substantially limit or minimize fluid communication between each of the first lumen 105 and/or the second lumen 106 with an exterior environment of the break-away connector 100 when the first and second body members 110, 120 are coupled to one another. For example, the seal member 132 may be configured to limit or minimize leakage of a fluid from within the break-away connector 100 to the exterior environment of the break-away connector 100. In certain embodiments, the seal member 132 may be an O-ring or another suitable sealing mechanism.

Figure 1D:
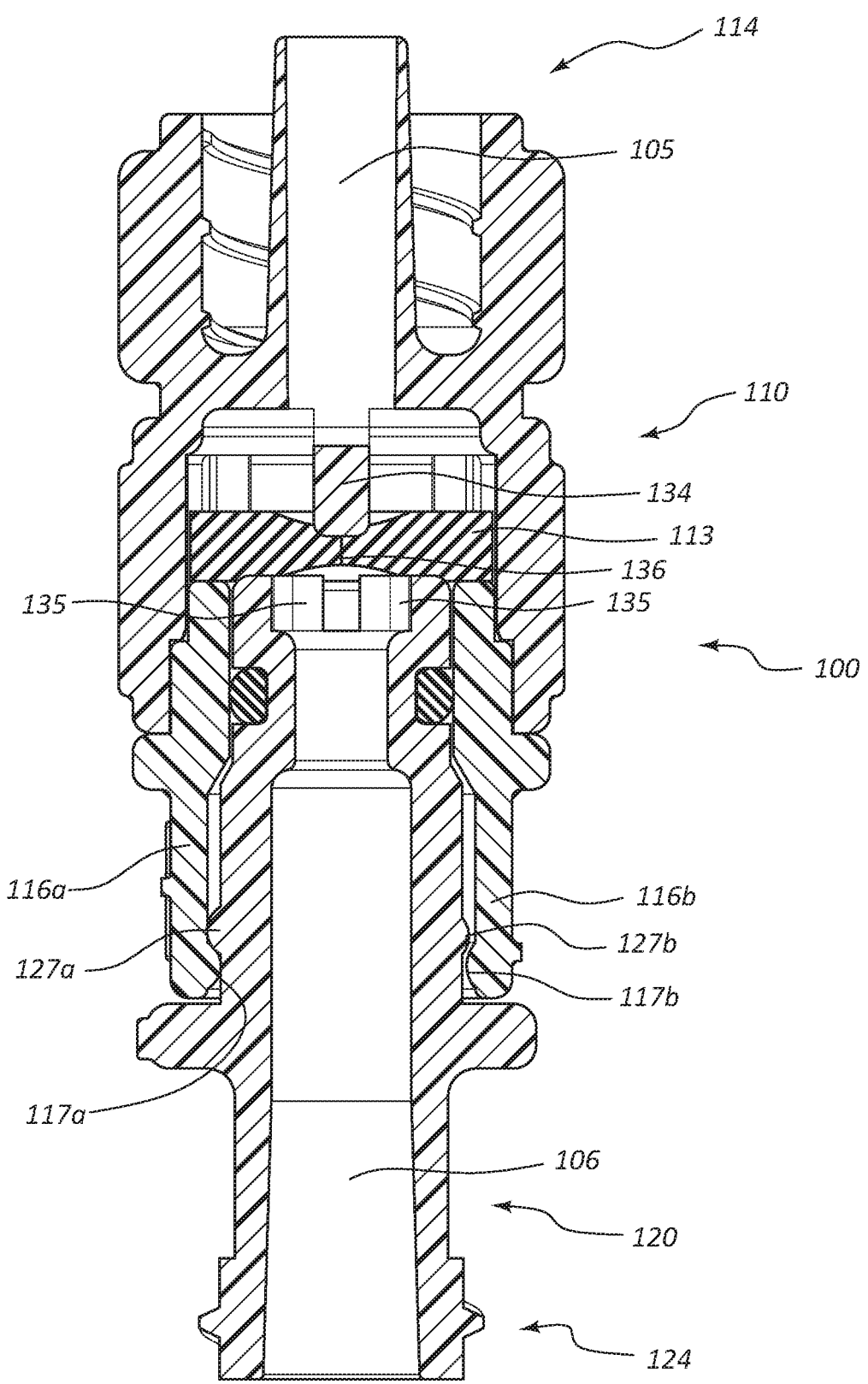
FIG. 1D is a cross-sectional side view of the break-away connector of FIG. 1A in the coupled state.

FIG. 1D is a cross-sectional side view of the break-away connector 100 of FIG. 1A in the coupled state. With reference to each of FIGS. 1C and 1D, the first body member 110 can comprise the first resilient arm 116a and the second resilient arm 116b. As illustrated, the height or profile of the first ridge portion 117a of the first resilient arm 116a can be greater than the height or profile of the second ridge portion 117b of the second resilient arm 116b. Likewise, the second body member 120 can comprise the first ridge portion 127a and the second ridge portion 127b, wherein the height or profile of the first ridge portion 127a can be greater than the height or profile of the second ridge portion 127b. As described above, the break-away connector 100 may comprise one, two, three, four, five, or more resilient arms, each resilient arm comprising a ridge portion. Additionally, the break-away connector 100 may comprise one, two, three, four, five, or more ridge portions of the second body member 120. Each of the plurality of ridge portions 117, 127 of the first body member 110 and/or the second body member 120, respectively, may have different heights or profiles and/or a combination of heights or profiles such that the break-away connector 100 may comprise a variety of coupling strengths or tightnesses. Accordingly, in certain embodiments, the break-away connector 100 may comprise one, two, three, four, five, or more coupling strength or tightness configurations.

In some embodiments, the first configuration may be a high force configuration. In the first configuration or the high force configuration, the first ridge portion 117a of the first resilient arm 116a may engage or interact with the first ridge portion 127a of the second body member 120 (the configuration shown in FIG. 1D). In such a configuration, two high profile ridge portions (e.g., the first ridge portions 117a, 127a) may engage or interact with each other. In certain embodiments, the second configuration may be a low force configuration. In the second configuration or the low force configuration, the first ridge portion 117a of the first resilient arm 116a may engage or interact with the second ridge portion 127b of the second body member 120. In such a configuration, a high profile ridge portion (e.g., the first ridge portion 117a) may engage or interact with a low profile ridge portion (e.g., the second ridge portion 127b). In certain embodiments, uncoupling of a break-away connector 100 when two high profile ridge portions are engaged with each other may utilize or require a greater force than uncoupling of the break-away connector 100 when a high profile ridge portion is engaged with a low profile ridge portion.

With reference again to FIGS. 1A and 1B, the first resilient arm 116a can comprise a first indicium 130a (e.g., an "H" for high or another suitable indicium), and a portion of the second body member 120 adjacent the first ridge portion 127a can comprise a second indicium 130b (e.g., an arrowhead or another suitable indicium). When the first indicium 130a and the second indicium 130b are substantially aligned (i.e., upon coupling of the first and second body members 110, 120) the break-away connector 100 can be in the high force configuration. Conversely, when the first indicium 130a is substantially aligned with a portion of the second body member 120 opposite of the second indicium 130b the break-away connector 100 can be in the low force configuration. Again, interaction of the one or more ribs 128a and a portion of the one or more slots 118a, 118b may facilitate alignment of the first body member 110 and the second body member 120 when coupled and when selecting between the high force configuration and the low force configuration.

Referring again to FIG. 1D, the valve 113 can be disposed within at least a portion of the first lumen 105. In some embodiments, the valve 113 may be disposed within at least a portion of the second lumen 106. In some other embodiments, a first valve may be disposed within the first lumen 105 and a second valve may be disposed within the second lumen 106.

As illustrated, the break-away connector 100 may comprise a first valve engagement member 134 disposed within the first lumen 105 and/or coupled to the first body member 110. The break-away connector 100 may also comprise a second valve engagement member 135 disposed within the second lumen 106 and/or coupled to the second body member 120. As illustrated, the first valve engagement member 134 comprises a post-like member configured to engage a center portion of a first surface of the valve 113. In some other embodiments, the first valve engagement member 134 may be substantially conical, substantially semi-spherical, or another suitable shape. In contrast, the second valve engagement member 135, as illustrated, comprises a raised, substantially annular surface configured to engage a portion of a second, or opposite, surface of the valve 113 disposed radially in relation to the center portion of the valve 113. In some embodiments, the second valve engagement member 135 may be substantially square, substantially triangular, or another suitable shape. The engagement or interaction of the first and second valve engagement members 134, 135 with the valve 113 may be configured to open the valve 113 when the first and second body members 110, 120 are coupled to one another. For example, the first and second valve engagement members 134, 135 may be displaced toward each other. The first valve engagement member 134 may be configured to displace the central portion of the valve 113 toward the second valve engagement member 135, and the second valve engagement member 135 may be configured to displace the portion of the valve radially disposed relative to the central portion of the valve 113 toward the first valve engagement member 134. Such displacement of the above-described portions of the valve 113 may result in the transition of the valve 113 from the closed configuration to the open configuration.

Other mechanisms of opening the valve 113 are also within the scope of this disclosure. For example, the break-away connector 100 may include only one valve engagement member (i.e., similar to the first valve engagement member 134). Engagement or interaction of the one such valve engagement member with the valve 113 may result in the transition of the valve 113 from the closed configuration to the open configuration. In certain embodiments, the valve 113 may be formed from a resilient material (e.g., a polymeric material or another suitable material) such that the valve 113 is also configured to transition from the open configuration to the closed configuration upon disengagement of the one or more valve engagement members 134, 135 from the valve 113. With reference to FIG. 1D, the valve 113 can further comprise an aperture 136, wherein the aperture 136 may be configured to transition from a closed configuration to an open configuration upon engagement between the one or more valve engagement members 134, 135 and the valve 113. Furthermore, the aperture 136 may also be configured to transition from the open configuration to the closed configuration upon disengagement of the one or more valve engagement members 134, 135 from the valve 113.

In various embodiments, the coupling end portion 114 of the first body member 110 may be configured to be coupled to a first medical device, and the coupling end portion 124 of the second body member 120 may be configured to be coupled to a second medical device. For example, as discussed above, the break-away connector 100 may be configured for use in medical procedures including, but not limited to, drainage of a volume of a fluid from a patient and intravenous feeding of a patient. The break-away connector 100 may be configured to be coupled to a fluid container such as an IV bag. The break-away connector 100 may also be configured to be coupled to a catheter, wherein at least a portion of the catheter is disposed in a patient at an access site. The break-away connector 100 may be configured to function or operate as a flow regulator in combination with an IV assembly. In some embodiments, the break-away connector 100 may be configured to adjust a rate of flow or passage of a fluid through the break-away connector 100. For example, the break-away connector 100 may further comprise a twist control mechanism or a needle valve.

In certain embodiments, each of the coupling end portions 114, 124 may comprise a different type of coupling mechanism. For example, the coupling end portion 114 may comprise a female connector and the coupling end portion 124 may comprise a male connector. In another example, the coupling end portion 114 may comprise a threaded coupling mechanism (e.g., a female connector or a male connector) and the coupling end portion 124 may comprise a compression fitting, a snap fitting, or another type of suitable fitting. In various other embodiments, each of the coupling end portions 114, 124 may comprise the same type of coupling mechanism. For example, each of the coupling end portions 114, 124 may comprise a female connector. In another example, each of the coupling end portions 114, 124 may comprise a male connector. In yet another example, each of the coupling end portions 114, 124 may comprise a compression fitting, a snap fitting, or another type of suitable fitting.

In some embodiments, the first body member 110 may be removably coupleable to the second body member 120 via a tether (not shown). For example, during packaging, shipment, and/or storage of the break-away connector 100 the first and second body members 110, 120 of the break-away connector 100 may be coupled to one another via a tether such that the first and second body members 110, 120 may not be separated and/or lost during packaging, shipment, and/or storage.

In another embodiment, the break-away connector 100 may comprise a pre-lock mechanism. For example, the second body member 120 may comprise one or more ridge portions or an annular ridge portion (not shown) that is configured to engage the ridge portions 117a, 117b of the one or more resilient arms 116a, 116b of the first body member 110. In some embodiments, a pre-lock ridge portion may be disposed such that the valve 113 is not disposed in an open configuration upon coupling of the first and second body members 110, 120 from or to the pre-lock configuration. Accordingly, the application or exertion of mechanical stress on the valve 113 may be limited or minimized during packaging, shipment, and/or storage.

The pre-lock ridge portion of the second body member 120 may have a lower height or profile than either of the ridge portions 127a, 127b, such that the resilient arms 116a, 116b are radially biased or extended outward from the longitudinal axis of the break-away connector 100 to a lesser degree or extent than when the ridge portions 117a, 117b of the resilient arms 116a, 116b are engaged with the ridge portions 127a, 127b of the second body member 120. Such a configuration may limit or minimize the mechanical stress applied to or exerted on the resilient arms 116a, 116b during packaging, shipment, and/or storage of the break-away connector 100 in a coupled state. For example, the pre-lock ridge portion may be configured such that the first and second body members 110, 120 may be coupled to one another while the resilient arms 116a, 116b may be only minimally or slightly biased or extended radially outward from the longitudinal axis of the break-away connector 100 during engagement into the pre-lock configuration.

FIGS. 2A-2D illustrate another embodiment of a break-away connector that can, in certain respects, resemble components of the break-away connector described in connection with FIGS. 1A-1D. It will be appreciated that all the illustrated embodiments may have analogous features. Accordingly, like features are designated with like reference numerals, with the leading digits incremented to "2." For instance, the first body member is designated as "110" in FIGS. 1A-1D, and an analogous first body member is designated as "210" in FIGS. 2A-2D. Relevant disclosure set forth above regarding similarly identified features thus may not be repeated hereafter. Moreover, specific features of the break-away connector and related components shown in FIGS. 1A-1D may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the break-away connector of FIGS. 2A-2D. Any suitable combination of the features, and variations of the same, described with respect to the break-away connector and components illustrated in FIGS. 1A-1D can be employed with the break-away connector and components of FIGS. 2A-2D, and vice versa. This pattern of disclosure applies equally to further embodiments depicted in subsequent figures and described hereafter.

Figure 2A:
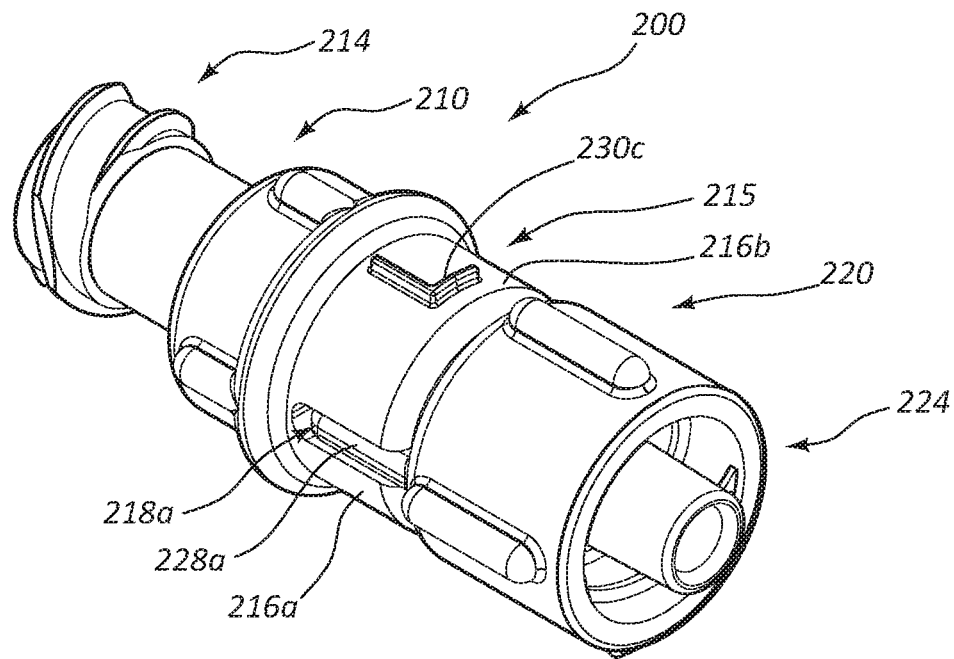
FIG. 2A is a perspective view of another embodiment of a break-away connector in a coupled state.
Figure 2B:
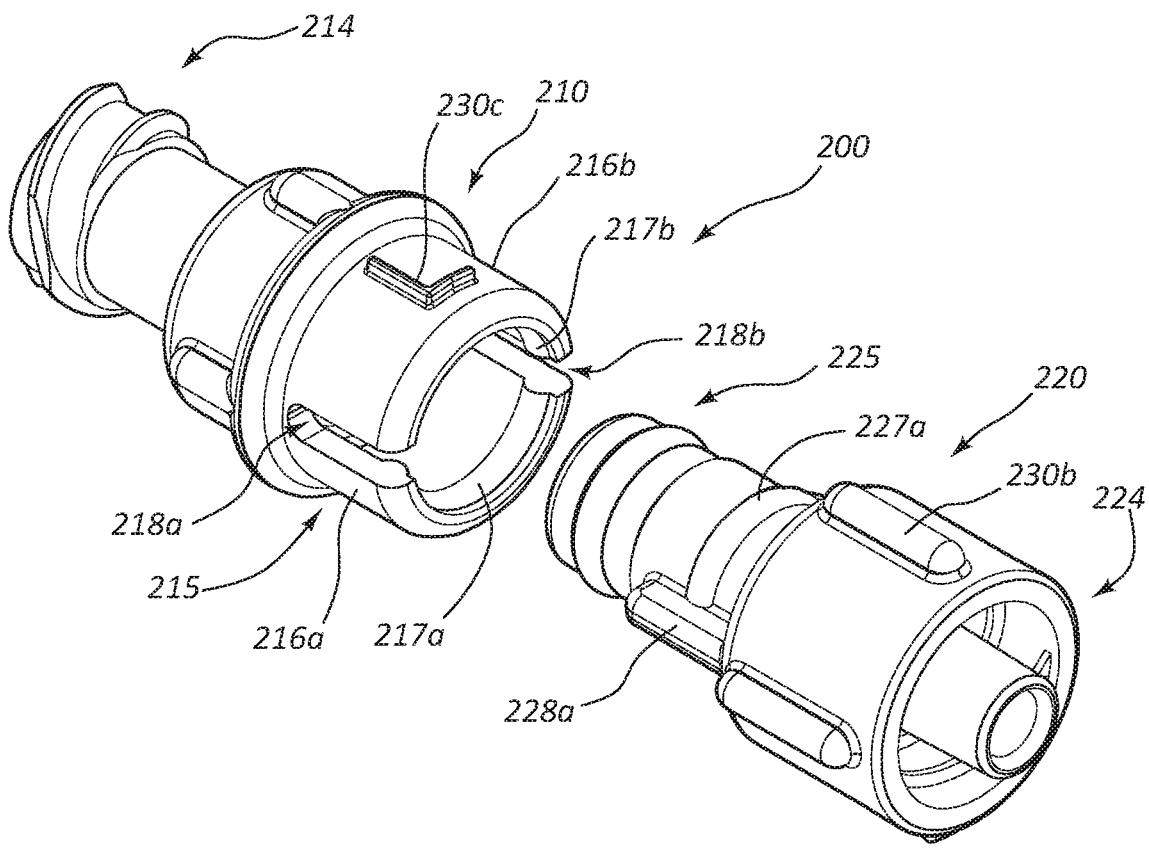
FIG. 2B is perspective view of the break-away connector of FIG. 2A in an uncoupled state.

FIG. 2A is a perspective view of a break-away connector 200 in a coupled state, and FIG. 2B is a perspective view of the break-away connector 200 of FIG. 2A in an uncoupled state. As illustrated, the break-away connector 200 can comprise a first body member 210 and a second body member 220. Analogous to the break-away connector 100 (see FIGS. 1A-1D), the first body member 210 can be coupled to the second body member 220, and vice versa. In contrast to the break-away connector 100, however, the break-away connector 200 as illustrated in FIG. 2B does not comprise a valve. In some embodiments, however, the break-away connector 200 may comprise one or more valves. For example, a first valve may be disposed within at least a portion of the first body member 210 and a second valve may be disposed within at least a portion of the second body member 220.

The first body member 210 can further comprise a coupling end portion 214 and a break-away end portion 215. The coupling end portion 214, as illustrated, comprises a female connector. As stated above, however, other suitable coupling mechanisms are also within the scope of this disclosure. The first body member 210 may further comprise one or more resilient arms, analogous to the resilient arms 116a, 116b. For example, the first body member 210 may comprise a first resilient arm 216a and a second resilient arm 216b. Furthermore, the one or more resilient arms 216a, 216b may comprise one or more ridge portions or raised portions. For example, the first resilient arm 216a can comprise a first ridge portion 217a and the second resilient arm 216b can comprise a second ridge portion 217b. Additionally, one or more slots (e.g., a first slot 218a and a second slot 218b) may be disposed adjacent, between, or within the one or more resilient arms 216a, 216b.

The second body member 220 can also comprise a coupling end portion 224 and a break-away end portion 225. As depicted, the coupling end portion 224 comprises a male connector. Again, as stated above, other suitable coupling mechanisms are also within the scope of this disclosure. The break-away end portion 225 of the second body member 220 can comprise one or more ridge portions or raised portions. For example, the break-away end portion 225 of the second body member 220 comprises a first ridge portion 227a and a second ridge portion 227b (see FIG. 2C). Furthermore, one or more ribs (e.g., a first rib 228a and a second rib disposed on an opposite side of the second body member 220 from the first rib 228a) may be disposed adjacent or between the one or more ridge portions 227a, 227b. In certain embodiments, the one or more ribs 228a may be configured to be at least partially disposed within at least a portion of the one or more slots 218a, 218b upon coupling of the first body member 210 and the second body member 220.

In various embodiments, the one or more ridge portions 217a, 217b of the first body member 210 may be configured to engage or interact with the one or more ridge portions 227a, 227b of the second body member 220 (i.e., upon coupling of the first and second body members 210, 220). Additionally, upon coupling of the first body member 210 with the second body member 220, the first and second body members 210, 220 may be coupleable in one of at least two configurations, as described above in reference to break-away connector 100. In some embodiments, a greater force may be utilized or required to uncouple the first and second body members 210, 220 when the break-away connector 200 is in a first configuration or a first setting in comparison to when the break-away connector 200 is in a second configuration or a second setting. For example, a practitioner uncoupling the first and second body members 210, 220 may apply, exert, or utilize a greater amount of force (i.e., mechanical force) to uncouple the first and second body members 210, 220 when the break-away connector 200 is in the first configuration in comparison to when the break-away connector 200 is in the second configuration.

Figure 2C:
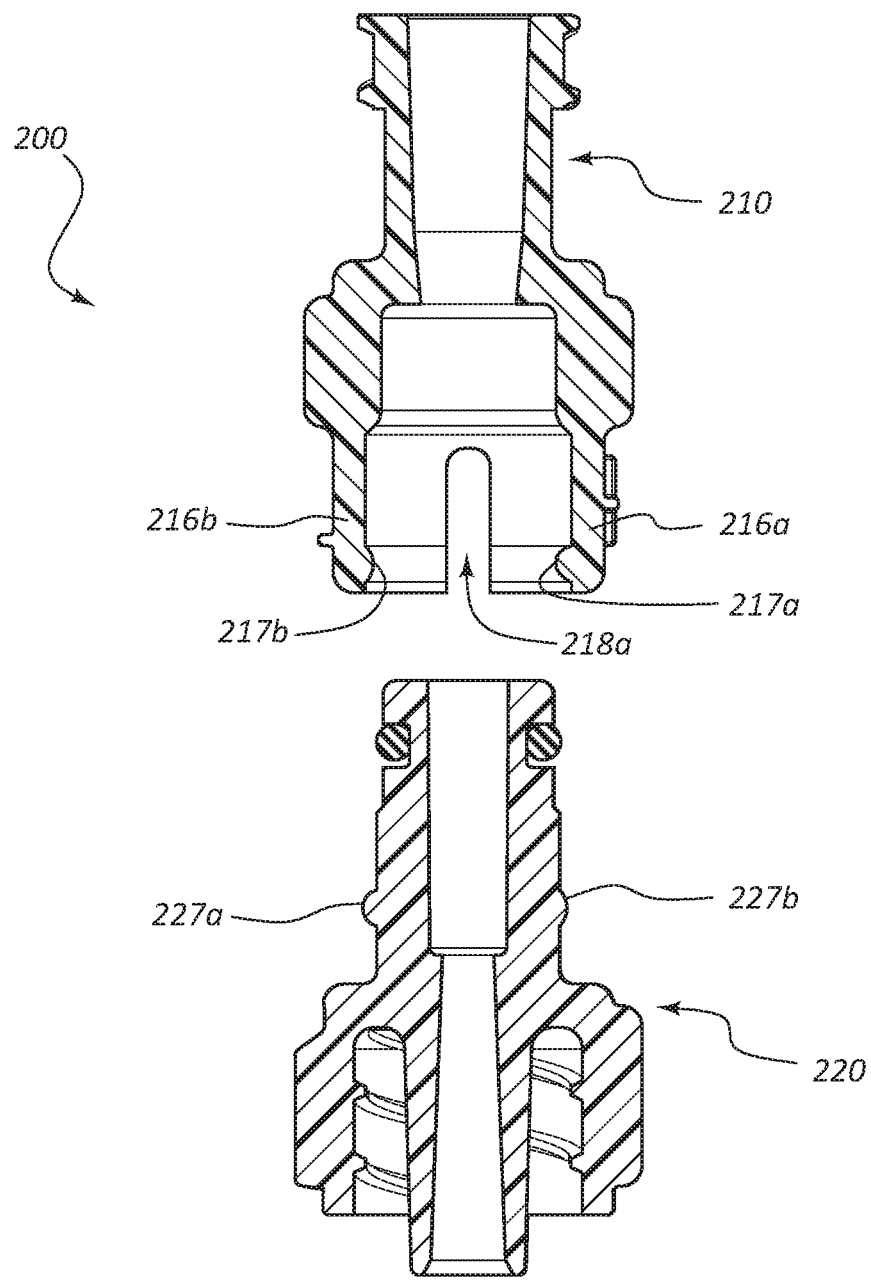
FIG. 2C is a cross-sectional side view of the break-away connector of FIG. 2A in the uncoupled state.

FIG. 2C is a cross-sectional side view of the break-away connector 200 of FIG. 2A in an uncoupled state. As depicted, the first body member 210 comprises the first resilient arm 216a and the second resilient arm 216b. As stated above, in some other embodiments, the first body member 210 may comprise one, two, three, four, five, or more resilient arms. The first slot 218a can be at least partially disposed between each of the first and second resilient arms 216a, 216b. As discussed above, the second body member 220 can comprise one or more ribs 228a (see FIG. 2A). In some embodiments, at least a portion of at least one of the ribs 228a can be configured to be disposed within at least a portion of each of the first and second slots 218a, 218b upon coupling of the first and second body members 210, 220. The disposition of at least a portion of the rib 228a within at least a portion of the slot 218a may be configured to substantially limit or minimize rotation of the first body member 210 in relation to the second body member 220 around a longitudinal axis of the break-away connector 200 when the first and second body members 210, 220 are coupled to one another. As stated above, the engagement or interaction of the first and second body members 210, 220 may substantially decrease or inhibit displacement or rotation of the first and second body members 210, 220 between each of the first configuration and the second configuration, and vice versa. This interaction may also facilitate alignment of the first body portion 210 and the second body portion 220 during coupling.

Figure 2D:
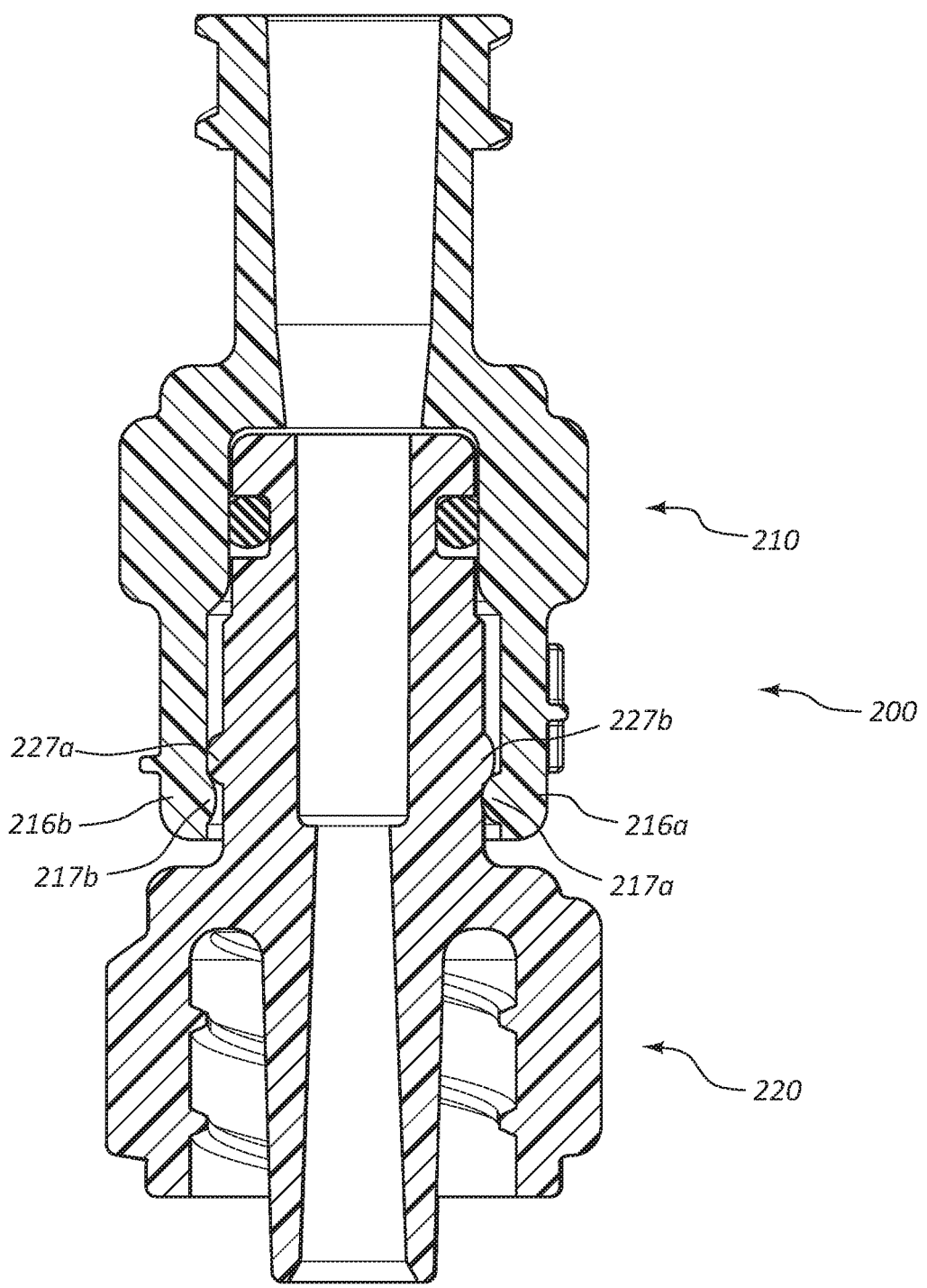
FIG. 2D is a cross-sectional side view of the break-away connector of FIG. 2A in the coupled state.

FIG. 2D is a cross-sectional side view of the break-away connector 200 of FIG. 2A in the coupled state. With reference to each of FIGS. 2C and 2D, the first body member 210 can comprise a first resilient arm 216a and a second resilient arm 216b. As illustrated, the height or profile of the first ridge portion 217a of the first resilient arm 216a can be greater than the height or profile of the second ridge portion 217b of the second resilient arm 216b. Likewise, the second body member 220 can comprise a first ridge portion 227a and a second ridge portion 227b, wherein the height or profile of the first ridge portion 227a can be greater than the height or profile of the second ridge portion 227b. As described above, the break-away connector 200 may comprise one, two, three, four, five, or more resilient arms, each resilient arm comprising a ridge portion. Additionally, the break-away connector 200 may comprise one, two, three, four, five, or more ridge portions of the second body member 220. Each of the plurality of ridge portions 217, 227 of the first body member 210 and/or the second body member 220, respectively, may have different heights or profiles and/or a combination of heights or profiles such that the break-away connector 200 may comprise a variety of coupling strengths or tightnesses. Accordingly, in certain embodiments, the break-away connector 200 may comprise one, two, three, four, five, or more coupling strength or tightness configurations.

As discussed above, the first configuration may be a high force configuration. In the first configuration or the high force configuration, the first ridge portion 217a of the first resilient arm 216a may engage or interact with the first ridge portion 227a of the second body member 220. In such a configuration, two high profile ridge portions (e.g., the first ridge portions 217a, 227a) may engage or interact with each other. In certain embodiments, the second configuration may be a low force configuration. In the second configuration or the low force configuration, as illustrated in FIG. 2D, the first ridge portion 217a of the first resilient arm 216a may engage or interact with the second ridge portion 227b of the second body member 220. In such a configuration, a high profile ridge portion (e.g., the first ridge portion 217a) may engage or interact with a low profile ridge portion (e.g., the second ridge portion 227b). In certain embodiments, uncoupling of a break-away connector 200 when a high profile ridge portion is engaged with a low profile ridge portion may utilize or require less force than uncoupling of the break-away connector 200 when two high profile ridge portions are engaged with one another.

With reference again to FIGS. 2A and 2B, the second resilient arm 216b can comprise a third indicium 230c (e.g., an "L" for low or another suitable indicium), while a portion of the second body member 220 adjacent the first ridge portion 227a can comprise a second indicium 230b (e.g., an arrowhead or another suitable indicium). When the second indicium 230b and the third indicium 230c are substantially aligned (i.e., upon coupling of the first and second body members 210, 220) the break-away connector 200 can be in the low force configuration, in contrast to the high force configuration depicted in FIGS. 1A and 1D. Each of the embodiments of FIGS. 1A-1D and FIGS. 2A-2D can be disposed in either a high force configuration or a low force configuration. In some embodiments, a different combination of indicia may be utilized to indicate different coupling configurations or settings of the break-away connector. For example, in embodiments comprising three or more resilient arms and/or ridge portions of the second body member, additional coupling configurations may be possible, wherein each configuration may comprise a different degree or level of coupling strength or tightness.

In certain embodiments, the first body member 210 may be formed from a first material and the second body member 220 may be formed from a second material. For example, the first body member 210 may be formed from a XENOY polymer blend and the second body member 220 may be formed from a material other than a XENOY polymer blend. A XENOY polymer blend may be partially or substantially resistant to cracking or deforming. For example, a body member formed from a XENOY polymer blend may be more durable (i.e., upon being cleaned or sterilized) than a body member formed from another material. Further, forming each of the first and second body members 210, 220 from different materials (i.e., a first material and a second material) may limit or minimize galling or binding between each of the first and second body members 210, 220. Other suitable materials and combinations of materials are also within the scope of this disclosure.

Figure 3A:
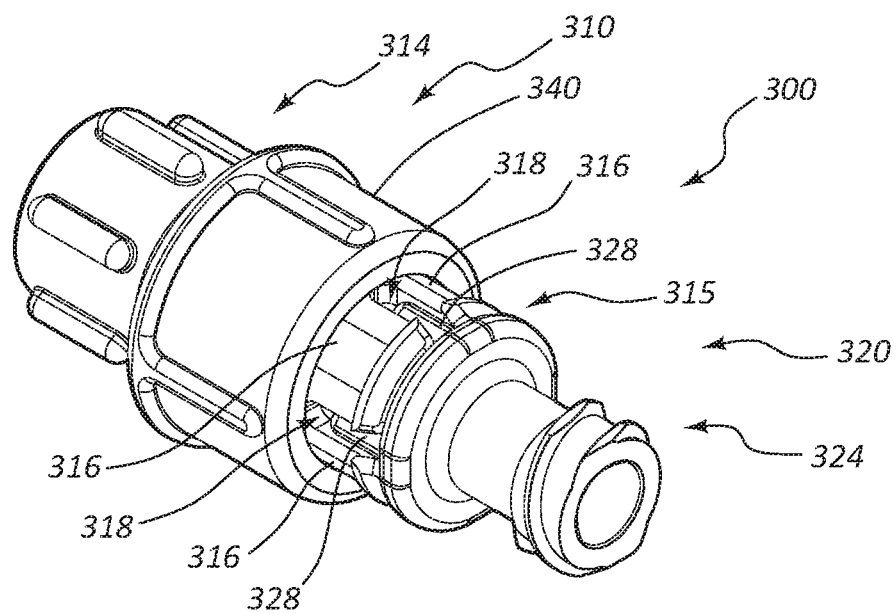
FIG. 3A is a perspective view of another embodiment of a break-away connector in a coupled state.
Figure 3B:
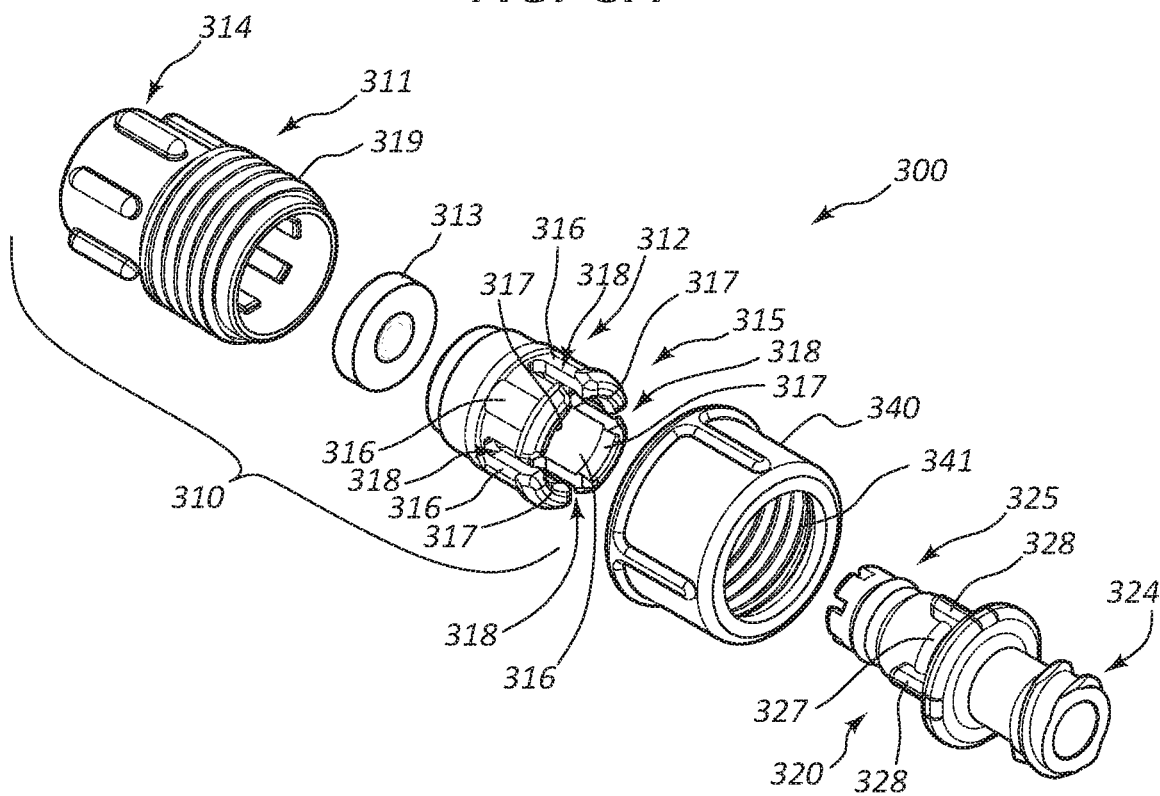
FIG. 3B is an exploded view of the break-away connector of FIG. 3A.

FIG. 3A is a perspective view of a break-away connector 300 in a coupled state, and FIG. 3B is an exploded view of the break-away connector 300 of FIG. 3A. As illustrated, the break-away connector 300 can comprise a first body member 310 and a second body member 320. Analogous to the break-away connectors 100, 200, the first and second body members 310, 320 of the break-away connector 300 are coupleable. Also, the uncoupled state of the break-away connector 300 corresponds to a state wherein the components of the first body member 310 are assembled but the first body member 310 and the second body member 320 are not coupled.

With reference to FIG. 3B, the first body member 310 may comprise a first portion 311, a second portion 312, and a valve 313. The valve 313 may be disposed within the first body member 310 (i.e., between each of the first portion 311 and the second portion 312). In some embodiments, the valve 313 may be disposed within the second body member 320. In some other embodiments, the break-away connector 300 may comprise more than one valve 313. For example, a first valve may be disposed within the first body member 310 and a second valve may be disposed within the second body member 320. As discussed above regarding the break-away connector 100, the first portion 311 and the second portion 312 may be coupled to each other by at least one of a compression fit, a snap fit, an adhesive, or another suitable coupling mechanism. In some embodiments, the first body member 310 may comprise only a single portion or another suitable number of portions.

The first body member 310, as shown, comprises a coupling end portion 314 and a break-away end portion 315. The coupling end portion 314 can be disposed at an end of the first body member 310 opposite from the break-away end portion 315. As illustrated, the coupling end portion 314 comprises a male connector. As stated above, however, other suitable coupling mechanisms are also within the scope of this disclosure. The first body member 310 can further comprise one or more resilient arms 316. For example, the first body member 310 can comprise four resilient arms 316. Furthermore, the one or more resilient arms 316 may comprise one or more ridge portions or raised portions 317. For example, a first resilient arm 316 can comprise a first ridge portion 317, a second resilient arm 316 can comprise a second ridge portion 317, and so on. Additionally, one or more slots 318 may be disposed adjacent, between, or within the one or more resilient arms 316.

The second body member 320 can also comprise a coupling end portion 324 and a break-away end portion 325, wherein the coupling end portion 324 can be disposed at an end of the second body member 320 opposite from the break-away end portion 325. As depicted, the coupling end portion 324 comprises a female connector. Again, as stated above, other suitable coupling mechanisms are also within the scope of this disclosure. The break-away end portion 325 of the second body member 320 can comprise one or more ridge portions or raised portions 327. For example, the break-away end portion 325 of the second body member 320 can comprise four ridge portions 327 disposed around at least a portion of the circumference of the break-away end portion 325. Furthermore, one or more ribs 328 can be disposed adjacent or between the one or more ridge portions 327. In certain embodiments, the one or more ribs 328 may be configured to be at least partially disposed within at least a portion of the one or more slots 318 upon coupling of the first and second body members 310, 320.

In various embodiments, the one or more ridge portions 317 of the first body member 310 may be configured to engage or interact with the one or more ridge portions 327 of the second body member 320 (i.e., upon coupling of the first and second body members 310, 320).

The break-away connector 300, as shown, can further comprise a collar member 340. As illustrated in FIG. 3B, the collar member 340 can include a plurality of threads 341, wherein the threads 341 are disposed on an interior surface of the collar member 340. Furthermore, the collar member 340 can be disposable around at least a portion of the first body member 310, wherein the plurality of collar member threads 341 may be configured to engage or interact with a plurality of threads 319 disposed on an exterior surface of the first portion 311 of the first body member 310. In some embodiments, the threads 319 may be disposed on a different portion of the first body member 310 (e.g., the second portion 312). In some other embodiments, a first portion of the threads 319 may be disposed on the first portion 311 and a second portion of the threads 319 may be disposed on the second portion 312. In yet some other embodiments, the threads 319, or at least a portion of the threads 319, may be disposed on the second body member 320 and the collar member 340 may be disposable around at least a portion of the second body member 320.

In certain embodiments, the collar member 340 may further comprise a first portion of a ratchet assembly (not shown). Furthermore, a second portion of the ratchet assembly may be disposed on at least a portion of the first body member 310 and/or the second body member 320. In some embodiments, a plurality of teeth of the first portion of the ratchet assembly may engage or interact with a plurality of detents of the second portion of the ratchet assembly, or vice versa. The ratchet assembly may aid in the continuous or incremental adjustment or tuning of the collar member 340, as discussed below. For example, rotation of the collar member 340 comprising a first or second portion of the ratchet assembly may generate one or more "clicks" that may be felt and/or heard by the user. Thus, the user may be able to adjust a degree or level of coupling strength of the break-away connector 300 according to rotating the collar member 340 through a desired or predetermined number of "clicks." In some embodiments, the ratchet assembly may limit or minimize accidental rotation of the collar member 340 and/or the ratchet assembly may limit or minimize rotation of the collar member 340 in at least one direction.

In various embodiments, the collar member 340 and/or the break-away connector 300 may comprise one or more indicia that may indicate or index the coupling strength or tightness configuration in which the break-away connector 300 is disposed. The collar member 340 may comprise an indicium (e.g., a tick mark) and a portion of the break-away connector 300 adjacent the collar member 340 may comprise a plurality of indicia that, when aligned with the indicium of the collar member 340, can indicate each of the plurality of coupling strengths of the break-away connector 300. For example, alignment of the indicium on the collar member 340 with a first indicium on a portion of the break-away connector 300 adjacent the collar member 340 may indicate that the break-away connector 300 is in a high force configuration, while alignment of the indicium on the collar member 340 with a fifth indicium on the portion of the break-away connector 300 adjacent the collar member 340 may indicate that the break-away connector 300 is in a high force configuration. Furthermore, alignment of the indicium on the collar member 340 with a second indicium, third indicium, or fourth indicium on the portion of the break-away connector 300 adjacent the collar member 340 can indicate that the break-away connector 300 is disposed in configurations of increasing tightness or strength, for example, from a first/low force configuration (e.g., setting "1") to a fifth/high force configuration (e.g., setting "5") and each of the incrementally increasing strengths in between (e.g., settings "2", "3", and "4"). Other numbers of indicia and/or settings are also within the scope of this disclosure. Such indicia that can indicate or index a coupling strength or tightness configuration in which a break-away connector is disposed may analogously and/or equally apply to all embodiments of the break-away connector as described herein (e.g., break-away connectors 300, 400, 600).

Figure 3C:
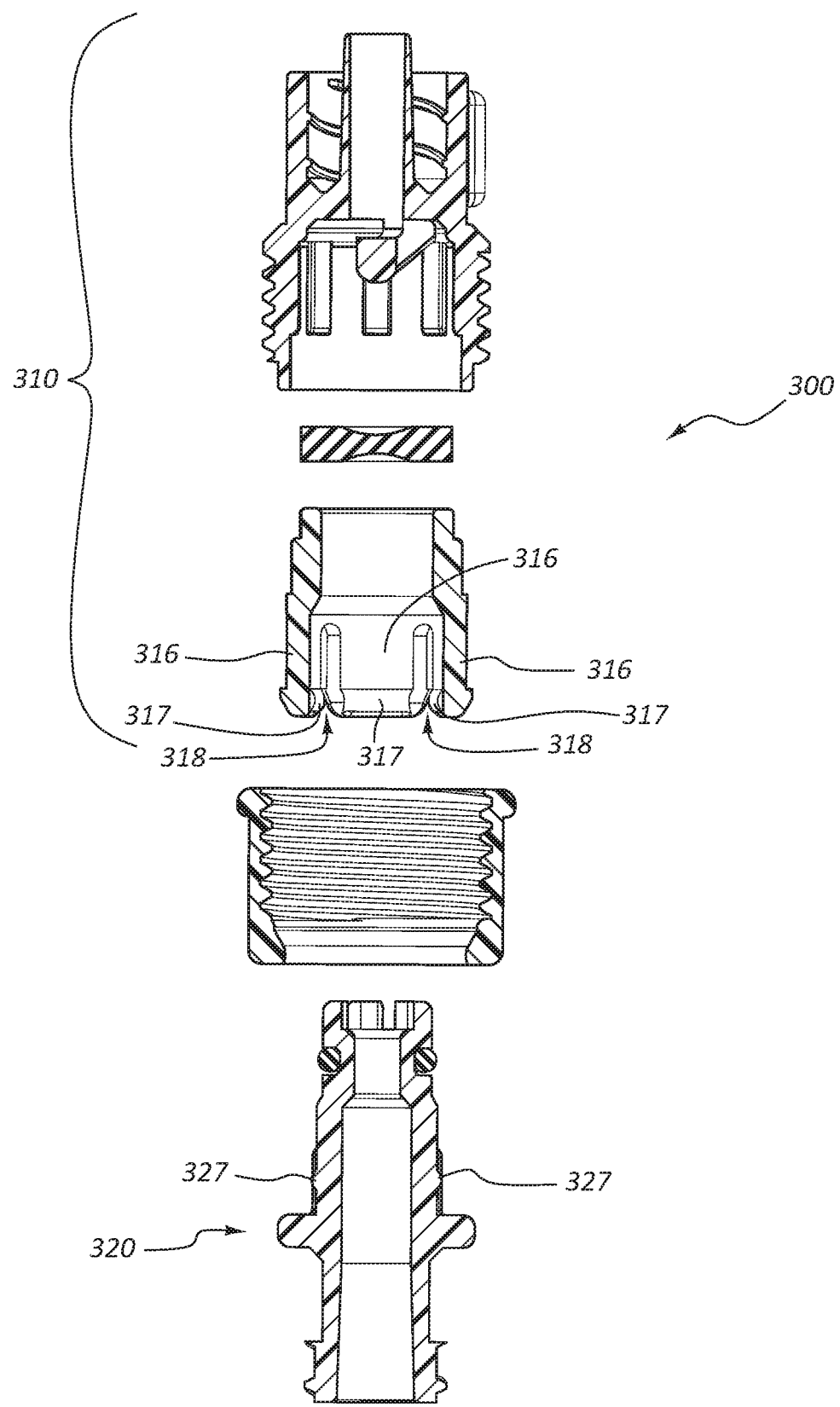
FIG. 3C is an exploded cross-sectional side view of the break-away connector of FIG. 3A.

FIG. 3C is an exploded cross-sectional side view of the break-away connector 300 of FIG. 3A. The first body member 310 comprises a plurality of resilient arms 316. As stated above, in some other embodiments, the first body member 310 may comprise one, two, three, four, five, six, or more resilient arms. A slot 318 can be at least partially disposed between each of the resilient arms 316. As discussed above, the second body member 320 can comprise one or more ribs 328 (see FIGS. 3A and 3B). In some embodiments, at least a portion of at least one of the ribs 328 can be configured to be disposed within at least a portion of the slots 318 upon coupling of the first and second body members 310, 320. The disposition of at least a portion of the rib 328 within at least a portion of at least one slot 318 may be configured to substantially limit or minimize rotation of the first body member 310 in relation to the second body member 320 around a longitudinal axis of the break-away connector 300 when the first and second body members 310, 320 are coupled to one another.

Figure 3D:
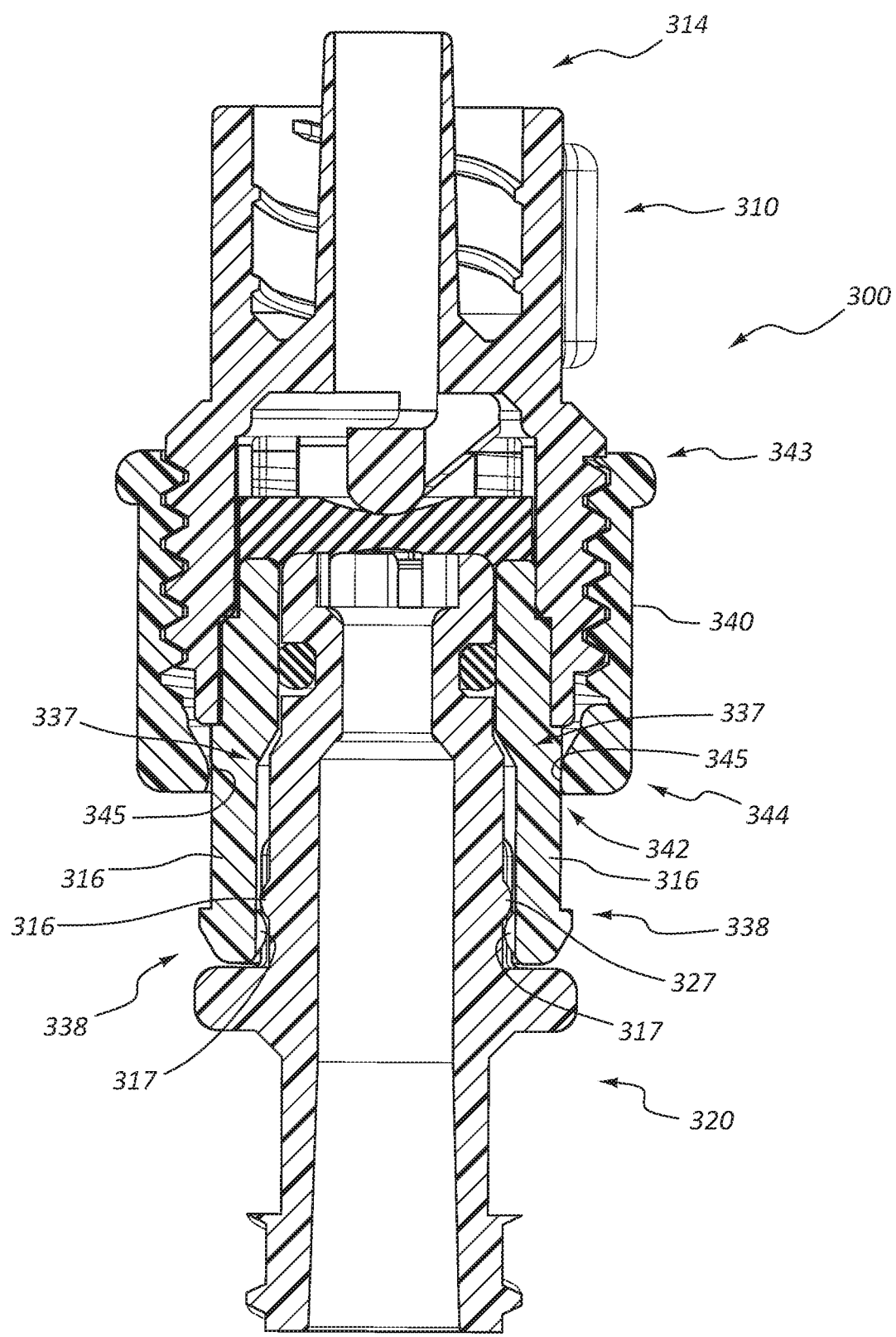
FIG. 3D is a cross-sectional side view of the break-away connector of FIG. 3A in the coupled state.

FIG. 3D is a cross-sectional side view of the break-away connector 300 of FIG. 3A, in the coupled state. With reference to each of FIGS. 3C and 3D, the first body member 310 can comprise a plurality of resilient arms 316, wherein each resilient arm 316 comprises a ridge portion 317. Likewise, the second body member 320 can comprise a plurality of ridge portions 327. As described above, the break-away connector 300 may comprise one, two, three, four, five, or more resilient arms, each resilient arm comprising a ridge portion. Additionally, the break-away connector 300 may comprise one, two, three, four, five, or more ridge portions 327 of the second body member 320. Each of the plurality of ridge portions 317, 327 of the first body member 310 and/or the second body member 320, respectively, may have different heights or profiles and/or a combination of heights or profiles such that the break-away connector 300 may comprise a variety of coupling strengths or tightnesses. Accordingly, in certain embodiments, the break-away connector 300 may comprise one, two, three, four, five, or more coupling strength or tightness configurations.

With continued reference to FIG. 3D, the collar member 340 may be configured to limit or minimize radial movement of the one or more resilient arms 316 outward relative to the longitudinal axis of the break-away connector 300. For example, as the collar member 340 is threadably rotated around at least a portion of the first body member 310, the collar member 340 can be displaced toward the coupling end portion 314 of the first body member 310 and consequently a lesser portion of the collar member 340 may be disposed at or adjacent the one or more resilient arms 316. As depicted, the collar member 340 comprises a first end portion 343 and a second end portion 344. The collar member 340 further comprises a lumen 342 disposed within the collar member 340 between at least the first end portion 343 and the second end portion 344. The diameter of the lumen 342 of the collar member 340 adjacent the first end portion 343, as shown, is greater than the diameter of the lumen 342 adjacent the second end portion 344. The interior surface of the collar member 340 adjacent the second end portion 344 can form a resilient arm engagement surface 345. When the resilient arm engagement surface 345 is disposed at or adjacent a base portion 337 of each of the resilient arms 316 (i.e., in a second position), as depicted in FIG. 3D, the length of the portion of each of the resilient arms 316 that is not disposed adjacent the interior surface of the collar member 340 is greater than when the collar member 340 is disposed at or adjacent an end portion 338 of each of the resilient arms 316 (i.e., in a first position). Stated another way, displacement of the collar member 340 longitudinally with respect to the resilient arms 316 may increase or decrease the effective length of the resilient arms 316.

The effective length of the resilient arms 316 may correlate to the force needed to couple or decouple the first body member 310 and the second body member 320. Interaction of the ridge portions 317 on the resilient arms 316 and the ridge portions 327 on the second body member 320 during coupling or uncoupling tend to displace the resilient arms 316 radially outward. The longer the effective length of the resilient arms 316, the relatively less force required to displace the ridge portions 317 of the resilient arms 316 radially outward. Shortening the effective length of the resilient arms 316 increases the necessary force. Thus displacement of the collar member 340 may allow for adjustment of the coupling or uncoupling force associated with the break-away connector 300, even in embodiments where the ridge portions 317 have a uniform height around the circumference of the first body member 310 and the ridge portions 327 of the second body member 320 have a uniform height around the circumference of the second body member 320.

Stated another way, the resilient arms 316 may be understood as cantilever springs, allowing for radial displacement to permit the ridge portions 317 of the resilient arms 316 to be displaced longitudinally past the ridge portions 327 of the second body member 320. The longer the effective length of the cantilever springs, the less force is needed to displace the free end of the cantilever spring a particular distance. Adjustment of the collar member 340 thus adjusts the effective length of the cantilever springs and thus adjusts the force needed to couple or decouple the break-away connector 300.

In the configuration as depicted in FIG. 3D (e.g., the second configuration or the second setting), wherein the resilient arm engagement surface 345 is disposed at or adjacent the base portion 337 of each of the resilient arms 316, each of the resilient arms 316 is less restricted and more freely able to be biased or to extend radially outward relative to the longitudinal axis of the break-away connector 300 such that each of the ridge portions 317 of the first body member 310 can be easily, or more easily, disengaged or uncoupled from the ridge portions 327 of the second body member 320. In contrast, when the resilient arm engagement surface 345 is disposed at or adjacent the end portion 338 of each of the resilient arms 316 (e.g., in the first configuration or the first setting), each of the resilient arms 316 is more restricted and less freely able to be biased or to extend radially outward relative to the longitudinal axis of the break-away connector 300, such that the ridge portions 317 of the first resilient arms 316 can be less easily disengaged or uncoupled from the ridge portions 327 of the second body member 320. Stated another way, it may be more difficult to disengage or uncouple the ridge portions 317 from the ridge portions 327 when the collar member 340 is in the first position compared to when the collar member 340 is in the second position.

In some embodiments, the collar member 340 may be continuously or incrementally adjustable between each of the first position and the second position such that the strength of the coupling of the first and second body members 310, 320, or a degree or level of coupling strength between the first and second body members 310, 320, is continuously or incrementally adjustable or tunable. In some embodiments, when the collar member 340 is in the first position the break-away connector 300 can be in the first configuration and when the collar member 340 is in the second position the break-away connector 300 can be in the second configuration. The first configuration, as described above, may be a high force configuration and the second configuration, as described above, may be a low force configuration. For example, a practitioner uncoupling the first and second body members 310, 320 may apply, exert, or utilize a greater amount of force (i.e., mechanical force) to uncouple the first and second body members 310, 320 when the break-away connector 300 is in the first configuration in comparison to when the break-away connector 300 is in the second configuration.

Figure 4A:
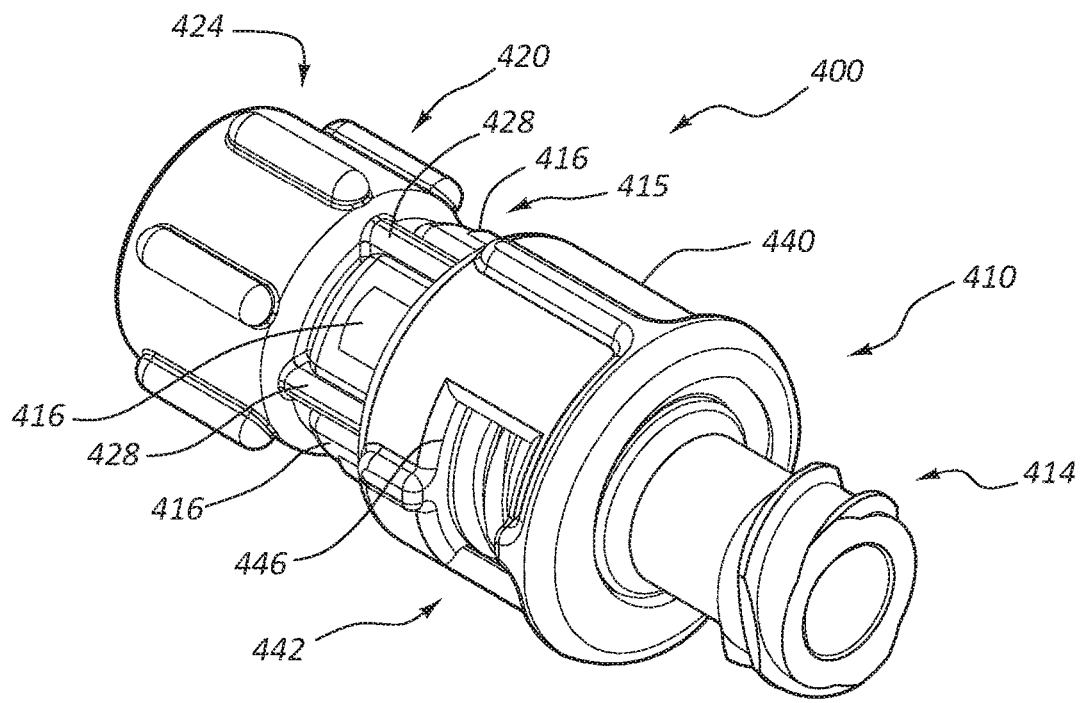
FIG. 4A is a perspective view of another embodiment of a break-away connector.
Figure 4B:
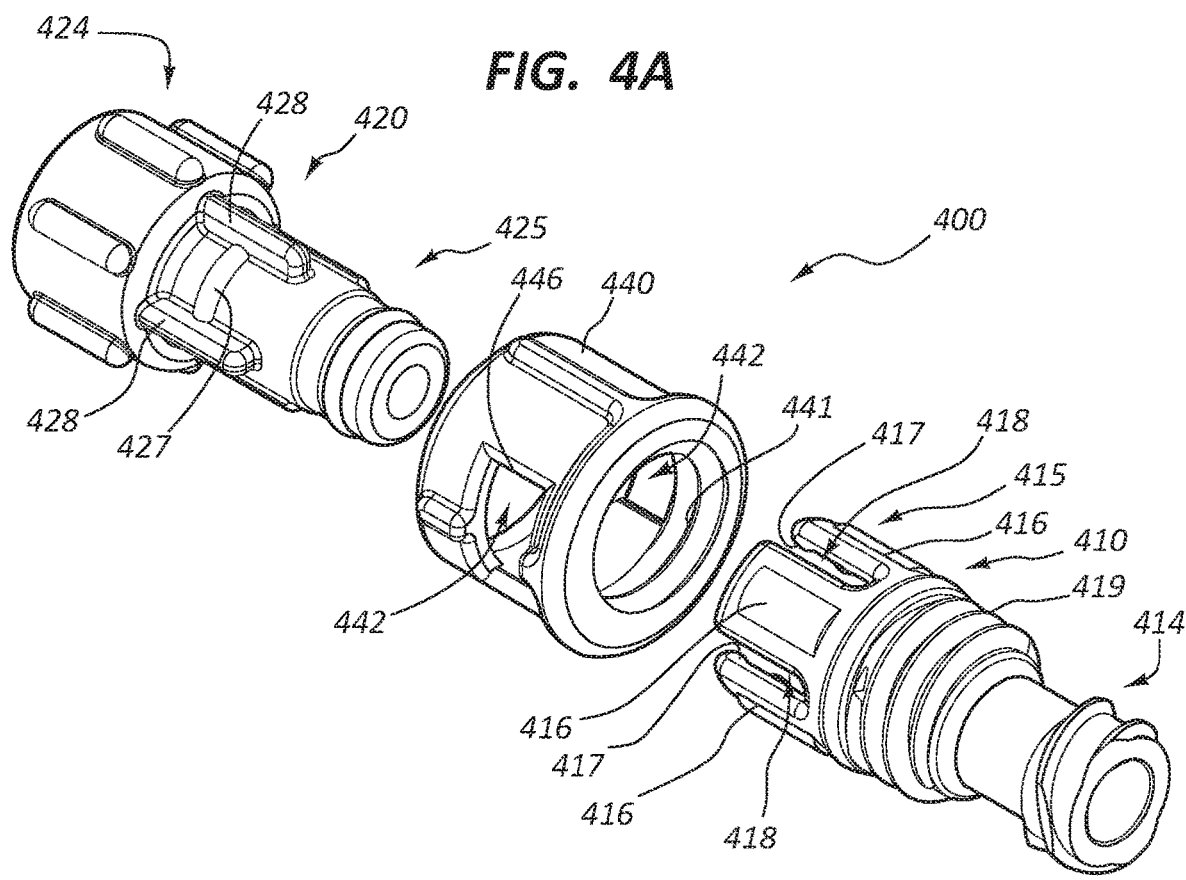
FIG. 4B is an exploded view of the break-away connector of FIG. 4A.

FIG. 4A is a perspective view of a break-away connector 400, in a coupled state, and FIG. 4B is an exploded view of the break-away connector 400 of FIG. 4A. As illustrated, the break-away connector 400 can comprise a first body member 410 and a second body member 420. Analogous to the break-away connectors 100, 200, 300, the first and second body members 410, 420 of the break-away connector 400 are coupleable. As discussed above in reference to the break-away connector 200, the break-away connector 400 does not include a valve. In some embodiments, however, the break-away connector 400 may comprise one or more valves. For example, a first valve may be disposed within at least a portion of the first body member 410 and a second valve may be disposed within at least a portion of the second body member 420.

The first body member 410, as shown, comprises a coupling end portion 414 and a break-away end portion 415. As illustrated, the coupling end portion 414 comprises a female connector. Again, as stated above, other suitable coupling mechanisms are also within the scope of this disclosure. The first body member 410 can further comprise one or more resilient arms 416. For example, the first body member 410 can comprise four resilient arms 416. Furthermore, the one or more resilient arms 416 may comprise one or more ridge portions or raised portions 417. For example, a first resilient arm 416 can comprise a first ridge portion 417, a second resilient arm 416 can comprise a second ridge portion 417, and so on. Additionally, one or more slots 418 may be disposed adjacent, between, or within the one or more resilient arms 416.

The second body member 420 can also comprise a coupling end portion 424 and a break-away end portion 425. As depicted, the coupling end portion 424 comprises a male connector. Again, as discussed above, other suitable coupling mechanisms are also within the scope of this disclosure. The break-away end portion 425 of the second body member 420 can comprise one or more ridge portions or raised portions 427. For example, the break-away end portion 425 of the second body member 420 can comprise four ridge portions 427 disposed around at least a portion of the circumference of the break-away end portion 425. Furthermore, one or more ribs 428 may be disposed adjacent or between the one or more ridge portions 427. In certain embodiments, the one or more ribs 428 may be configured to be at least partially disposed within at least a portion of the one or more slots 418 upon coupling of the first and second body members 410, 420.

In various embodiments, the one or more ridge portions 417 of the first body member 410 may be configured to engage or interact with the one or more ridge portions 427 of the second body member 420 (i.e., upon coupling of the first and second body members 410, 420).

The break-away connector 400, as shown, can further comprise a collar member 440. As illustrated in FIG. 4B, the collar member 440 can include a plurality of threads 441, wherein the threads 441 are disposed on an interior surface of the collar member 440. Furthermore, the collar member 440 is disposable around at least a portion of the first body member 410, wherein the plurality of collar member threads 441 may be configured to engage or interact with a plurality of threads 419 disposed on an exterior surface of the first body member 410. In some embodiments, the threads 419 may be disposed on a different portion of the first body member 410. In some other embodiments, the threads 419, or at least a portion of the threads 419, may be disposed on the second body member 420 and the collar member 440 may be disposable around at least a portion of the second body member 420 or each of the first and second body members 410, 420.

In some embodiments, the collar member 440 may further comprise one or more openings or windows 446. The openings 446 may allow or permit a user to access or view various components of the break-away connector 400 that are disposed in at least a portion of a lumen 442 of the collar member 440. In some embodiments, such a configuration may aid a user in adjusting or tuning a coupling strength of the break-away connector 400.

Figure 4C:
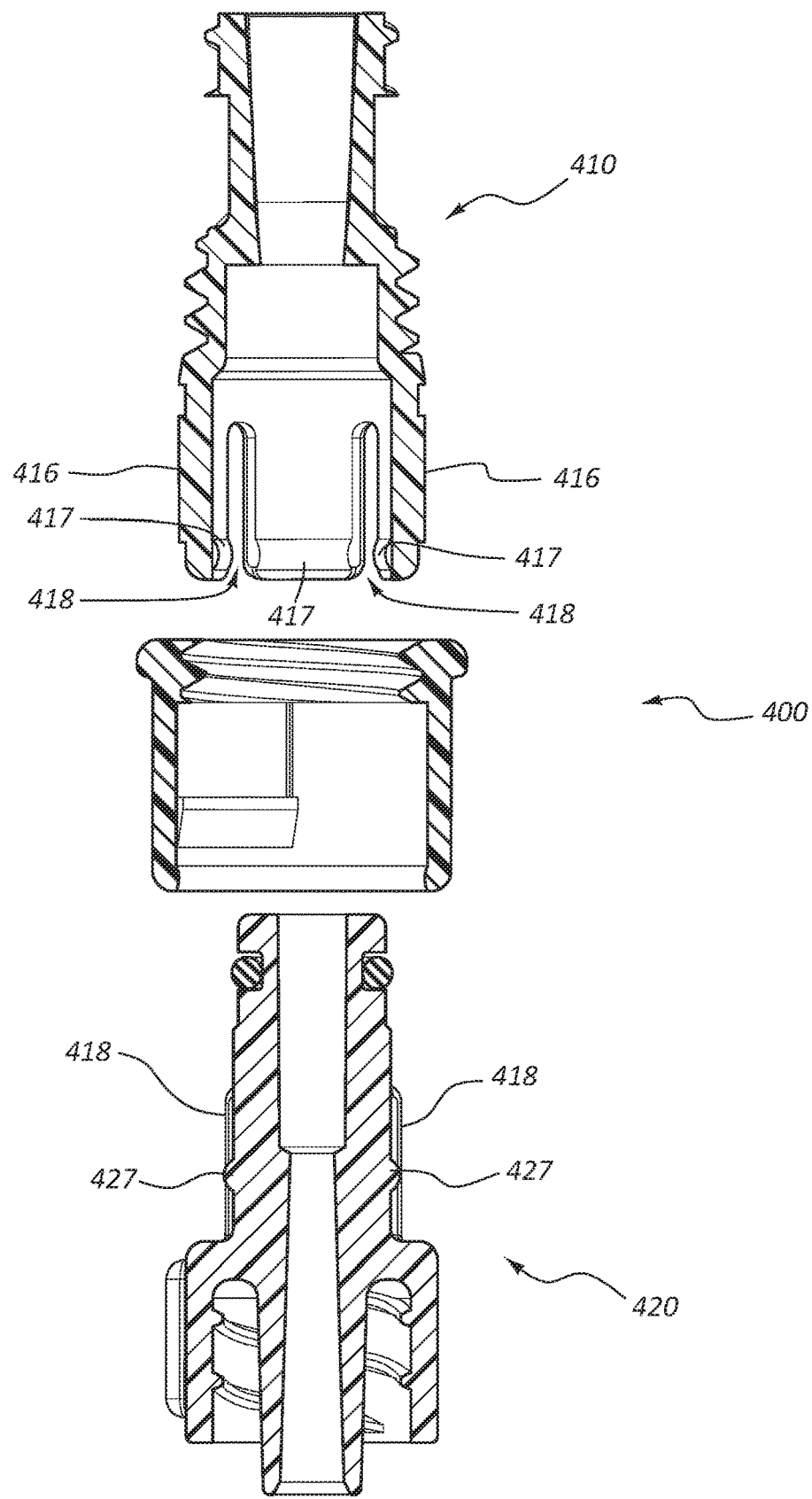
FIG. 4C is an exploded cross-sectional side view of the break-away connector of FIG. 4A.

FIG. 4C is an exploded cross-sectional side view of the break-away connector 400 of FIG. 4B. As depicted, the first body member 410 comprises a plurality of resilient arms 416. As stated above, in some other embodiments, the first body member 410 may comprise one, two, three, four, five, six, or more resilient arms. A slot 418 can be at least partially disposed between two of the resilient arms 416. As discussed above, the second body member 420 can comprise a plurality of ribs 428. In some embodiments, at least a portion of at least one of the ribs 428 can be configured to be disposed within at least a portion of at least one of the slots 418 upon coupling of the first and second body members 410, 420. The disposition of at least a portion of the rib 428 within at least a portion of at least one slot 418 may be configured to substantially limit or minimize rotation of the first body member 410 in relation to the second body member 420 around a longitudinal axis of the break-away connector 400 when the first and second body members 410, 420 are coupled to one another.

Figure 4D:
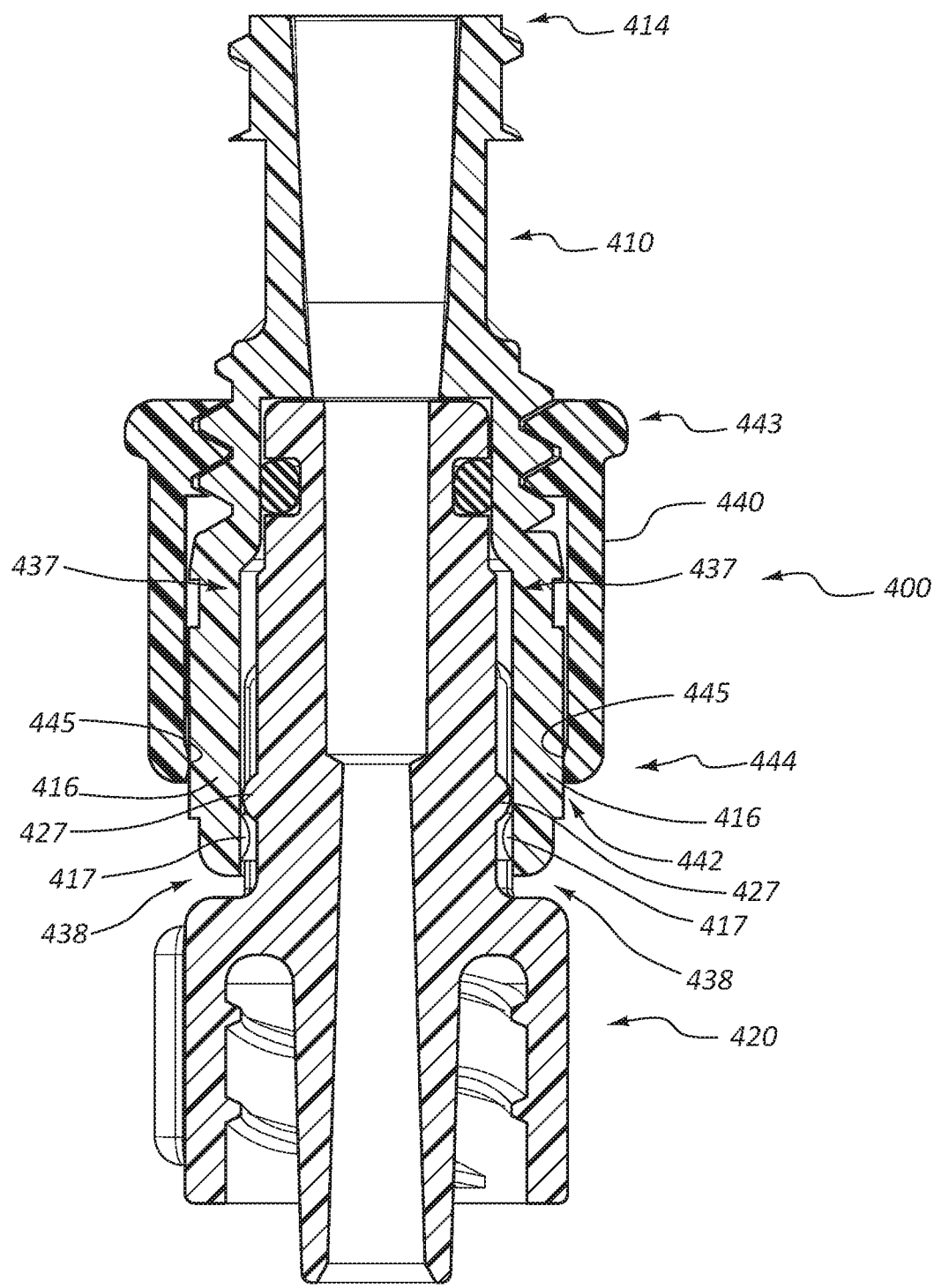
FIG. 4D is a cross-sectional side view of the break-away connector of FIG. 4A in the coupled state.

FIG. 4D is a cross-sectional side view of the break-away connector 400 of FIG. 4A, in the coupled state. With reference to each of FIGS. 4C and 4D, the first body member 410 can comprise a plurality of resilient arms 416, wherein each resilient arm 416 comprises a ridge portion 417. Likewise, the second body member 420 can comprise a plurality of ridge portions 427. As described above, the break-away connector 400 may comprise one, two, three, four, five, or more resilient arms, each resilient arm comprising a ridge portion. Additionally, the break-away connector 400 may comprise one, two, three, four, five, or more ridge portions 427 of the second body member 420. Each of the plurality of ridge portions 417, 427 of the first body member 410 and/or the second body member 420, respectively, may have different heights or profiles and/or a combination of heights or profiles such that the break-away connector 400 may comprise a variety of coupling strengths or tightnesses. Accordingly, in certain embodiments, the break-away connector 400 may comprise one, two, three, four, five, or more coupling strength or tightness configurations.

With continued reference to FIG. 4D, the collar member 440 may be configured to limit or minimize radial movement of the one or more resilient arms 416 outward relative to the longitudinal axis of the break-away connector 400. For example, as the collar member 440 is threadably rotated around the first body member 410, the collar member 440 may be displaced toward the coupling end portion 414 of the first body member 410 and consequently a lesser portion of the collar member 440 may be disposed at or adjacent the one or more resilient arms 416. As depicted, the collar member 440 comprises a first end portion 443 and a second end portion 444. The collar member 440 further comprises a lumen 442 disposed within the collar member 440 between at least the first end portion 443 and the second end portion 444. The interior surface of the collar member 440 adjacent the first end portion 443 can form a resilient arm engagement surface 445. When the resilient arm engagement surface 445 is disposed at or adjacent a base portion 437 of each of the resilient arms 416 (i.e., in a second position), the length of the portion of each of the resilient arms 416 that is not disposed adjacent an interior surface of the collar member 440 is greater than when the collar member 440 is disposed at or adjacent an end portion 438 of each of the resilient arms 416 (i.e., in a first position).

In the second configuration or the second setting, wherein the resilient arm engagement surface 445 is disposed at or adjacent the base portion 437 of each of the resilient arms 416, each of the resilient arms 416 is less restricted and more freely able to be biased or to extend radially outward relative to the longitudinal axis of the break-away connector 400 such that each of the ridge portions 417 of the first body member 410 can be easily, or more easily, disengaged or uncoupled from the ridge portions 427 of the second body member 420. In contrast, when the resilient arm engagement surface 445 is disposed at or adjacent the end portion 438 of each of the resilient arms 416 (e.g., in the first configuration or the first setting), each of the resilient arms 416 is more restricted and less freely able to be biased or to extend radially outward relative to the longitudinal axis of the break-away connector 400, such that the ridge portions 417 of the first resilient arms 416 can be less easily disengaged or uncoupled from the ridge portions 427 of the second body member 420. Stated another way, it may be more difficult to disengage or uncouple the ridge portions 417 from the ridge portions 427 when the collar member 440 is in the first position compared to when the collar member 440 is in the second position.

Analogous to the embodiment of FIGS. 3A-3D, adjustment of the collar member 440 may thus adjust the effective length of the resilient arms 416 to adjust the force associated with coupling or uncoupling the break-away connector 400.

In some embodiments, the collar member 440 may be continuously or incrementally adjustable between each of the first position and the second position such that the strength of the coupling of the first and second body members 410, 420, or a level of coupling strength between the first and second body members 410, 420, is continuously or incrementally adjustable or tunable. In some embodiments, when the collar member 440 is in the first position the break-away connector 400 can be in the first configuration and when the collar member 440 is in the second position the break-away connector 400 can be in the second configuration. The first configuration, as described above, may be a high force configuration and the second configuration, as described above, may be a low force configuration. For example, a practitioner uncoupling the first and second body members 410, 420 may apply, exert, or utilize a greater amount of force (i.e., mechanical force) to uncouple the first and second body members 410, 420 when the break-away connector 400 is in the first configuration in comparison to when the break-away connector 400 is in the second configuration.

Figure 5A:
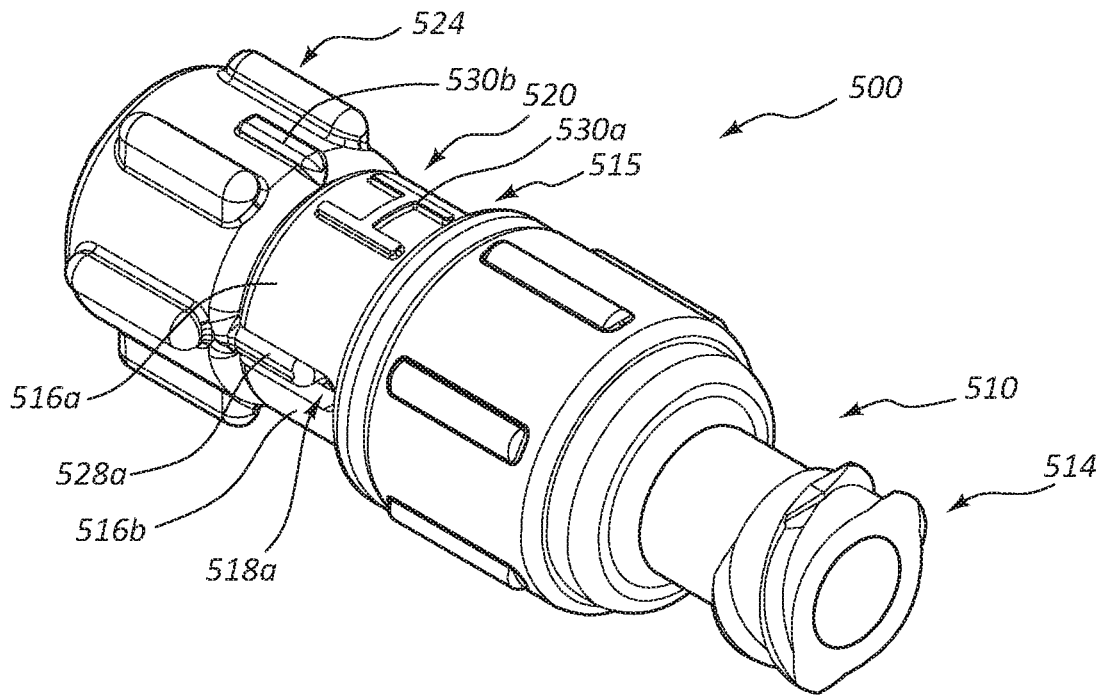
FIG. 5A is a perspective view of another embodiment of a break-away connector in a coupled state.
Figure 5B:
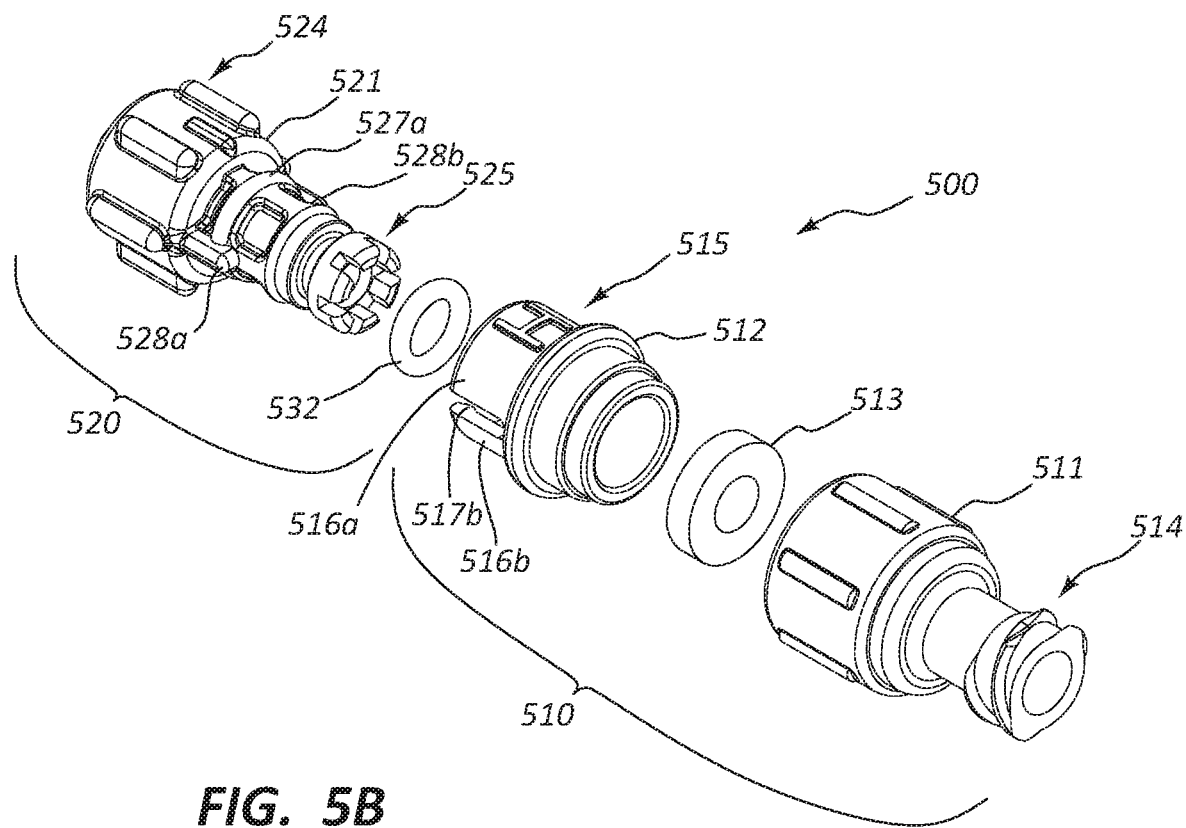
FIG. 5B is an exploded view of the break-away connector of FIG. 5A.

FIG. 5A is a perspective view of a break-away connector 500 in a coupled state, and FIG. 5B is an exploded view of the break-away connector 500 of FIG. 5A. As illustrated, the break-away connector 500 can comprise a first body member 510 and a second body member 520. Analogous to the break-away connectors 100, 200, 300, 400, the first and second body members 510, 520 of the break-away connector 500 are coupleable. Also, the uncoupled state of the break-away connector 500 corresponds to a state wherein the components of each of the first body member 510 and the second body member 520 are assembled but the first body member 510 and the second body member 520 are not coupled. In comparison to the break-away connector 100, for example, the polarity of the valve 513 and the coupling end portions 514, 524 of the break-away connector 500 is switched or inverted.

Figure 5C:
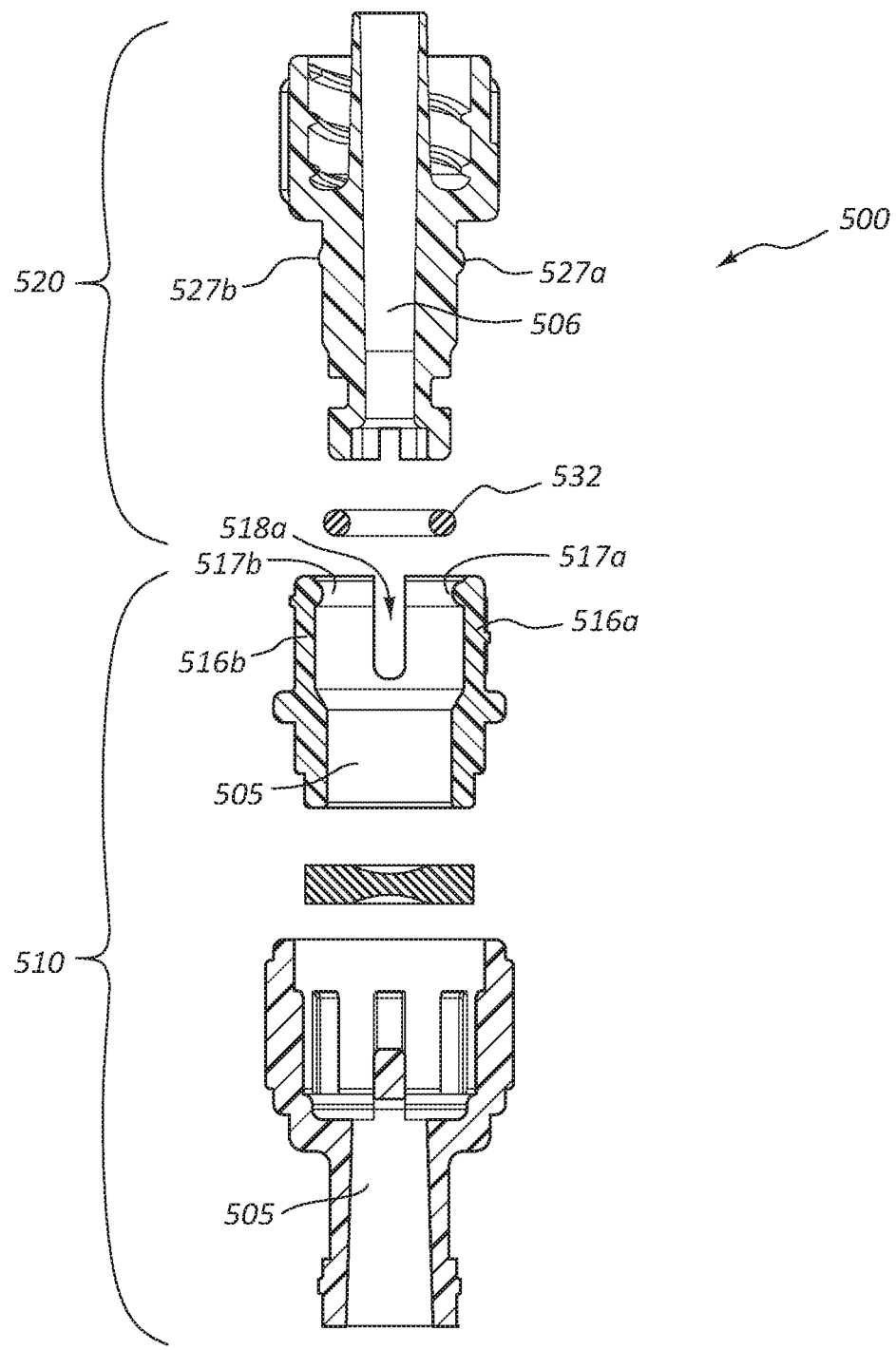
FIG. 5C is an exploded cross-sectional side view of the break-away connector of FIG. 5A.
Figure 5D:
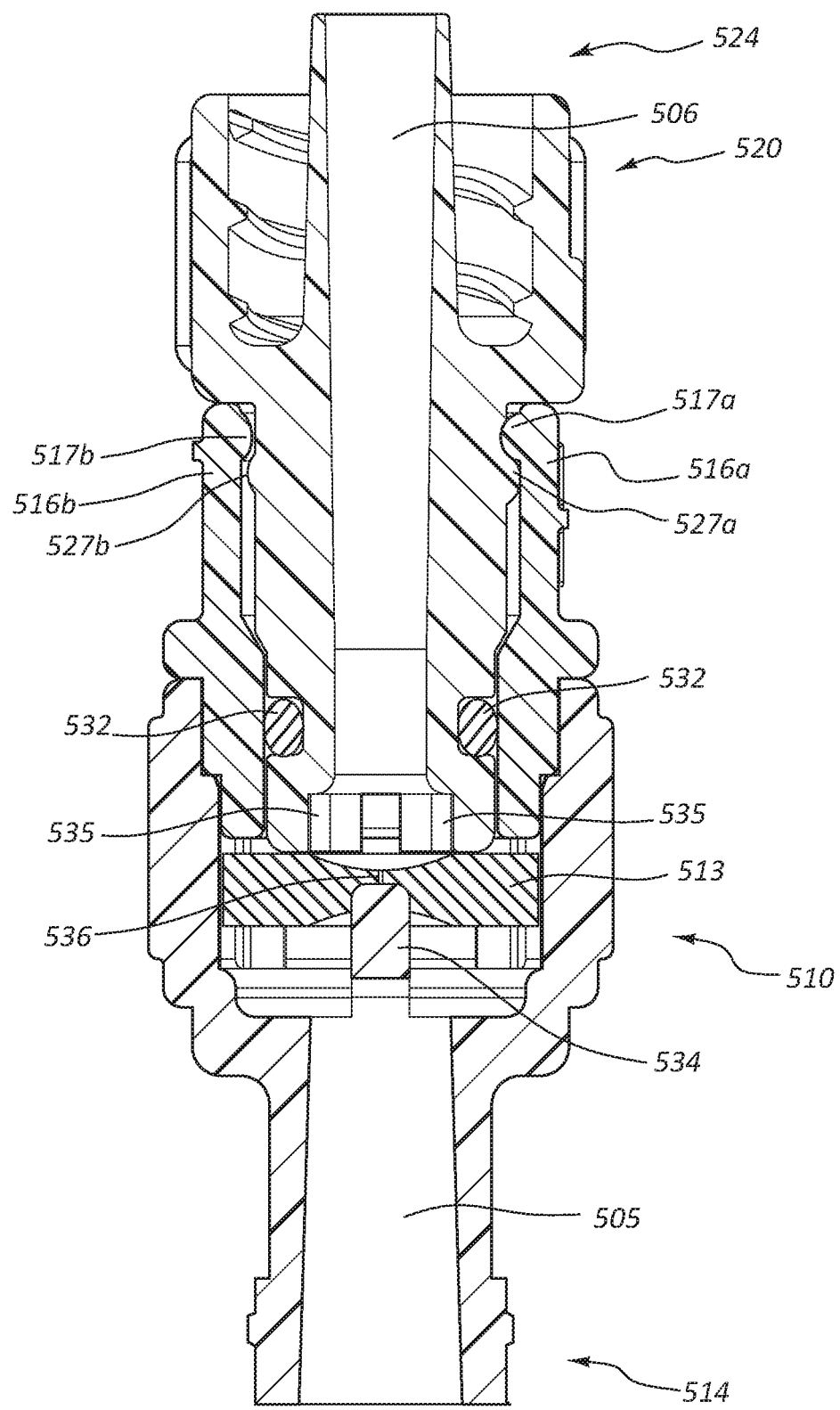
FIG. 5D is a cross-sectional side view of the break-away connector of FIG. 5A in the coupled state.

Again, in some embodiments, the first body member 510 can be coupled to the second body member 520, and vice versa, by a user. With reference to FIG. 5B, the first body member 510 may comprise a first portion 511, a second portion 512, and a valve 513. The valve 513 may be disposed within the first body member 510 (i.e., between each of the first portion 511 and the second portion 512). As discussed above regarding the break-away connectors 100, 300, the first portion 511 and the second portion 512 may be coupled to each other by at least one of a compression fit, a snap fit, an adhesive, or another suitable coupling mechanism. The second body member 520 may comprise a first portion 521 and a seal member 532. The seal member 532 may be configured to be coupled to the first portion 521 as illustrated in FIGS. 5C and 5D. In some embodiments, the first body member may comprise only a single portion or another suitable number of portions. In certain embodiments, the second body member may comprise two portions or another suitable number of portions.

The first body member 510 can further comprise a coupling end portion 514 and a break-away end portion 515. As depicted, the coupling end portion 514 may be disposed at an end of the first body member 510 opposite from the break-away end portion 515. The coupling end portion 514, as illustrated, comprises a female connector. As discussed above, however, the coupling end portion 514 may comprise any suitable coupling mechanism. The first body member 510 may further comprise one or more resilient arms. For example, the first body member 510 may comprise a first resilient arm 516a and a second resilient arm 516b, wherein the resilient arms 516a, 516b extend longitudinally away from the coupling end portion 514 of the first body member 510. Furthermore, the one or more resilient arms 516a, 516b may comprise one or more ridge portions or raised portions. For example, the first resilient arm 516a may comprise a first ridge portion 517a (see FIGS. 5C and 5D) extending inwardly toward a longitudinal axis of the break-away connector 500, and the second resilient arm 516b may comprise a second ridge portion 517b extending inwardly toward the longitudinal axis of the break-away connector 500. One or more slots may be disposed adjacent, between, or within the one or more resilient arms 516a, 516b. For example, as illustrated, a first slot 518a and a second slot (not visible in this view) can be disposed between each of the first resilient arm 516a and the second resilient arm 516b. In some embodiments, the break-away connector 500 may comprise one, two, three, four, five, or more resilient arms, ridge portions, and/or slots.

The second body member 520 can also comprise a coupling end portion 524 and a break-away end portion 525, wherein the coupling end portion 524 may be disposed at an end of the second body member 520 opposite from the break-away end portion 525. The coupling end portion 524, as illustrated, comprises a male connector. Again, as discussed above, the coupling end portion 524 may also comprise any suitable coupling mechanism. The break-away end portion 525 of the second body member 520 can comprise one or more ridge portions or raised portions. For example, the break-away end portion 525 can comprise a first ridge portion 527a and a second ridge portion 527b (see FIGS. 5C and 5D). One or more ribs may also be disposed adjacent or between the one or more ridge portions 527a, 527b. For example, the break-away end portion 525 may comprise a first rib 528a and a second rib 528b. In certain embodiments, the one or more ribs 528a, 528b may be configured to be at least partially disposed within at least a portion of the one or more slots 518a upon coupling of the first and second body portions 510, 520.

In various embodiments, the one or more ridge portions 517a, 517b of the first body member 510 may be configured to engage or interact with the one or more ridge portions 527a, 527b of the second body member 520. Additionally, the first and second body members 510, 520 may be coupleable in at least two configurations or settings. In some embodiments, a greater force may be required to uncouple the first body member 510 from the second body member 520 when the break-away connector 500 is in a first configuration or setting in comparison to when the break-away connector 500 is in a second configuration or setting. For example, a practitioner uncoupling the first body member 510 from the second body member 520 may apply, exert, or utilize a greater amount of force (i.e., mechanical force) to uncouple the first body member 510 from the second body member 520 when the break-away connector 500 is in the first configuration than when the break-away connector 500 is in the second configuration. In some other embodiments, the first and second body members 510, 520 may be coupleable in three, four, five, or more configurations or settings, wherein each configuration or setting may comprise a different level of strength or tightness.

As stated above, the polarity of the valve 513 and the coupling end portions 514, 524 of the break-away connector 500 can be switched or inverted in comparison to the break-away connector 100. In some embodiments, the first body member 512, which comprises the valve 513, may be coupled (e.g., by a practitioner or a user) more proximally than the second body member 520 to a medical device such as a drainage bag or a collection bag. When the break-away connector 500 is in use (i.e., coupled to a patient via a catheter to drain a volume of a fluid from the patient), the valve 513 may be disposed in the first body member 512. Stated another way, the valve 513 may be disposed on the drainage bag "side" of the break-away connector 500. In contrast, a first end of a catheter can be coupled to the second body member 520 and a second end of the catheter can be coupled to or disposed within a patient. Stated another way, the catheter may be disposed on the patient "side" of the break-away connector 500. In such a configuration, the catheter may continue to drain fluid from the patient (i.e., onto the floor) even if the first body member 510 and the second body member 520 of the break-away connector 500 decouple.

In some other embodiments, the first body member 512, which comprises the valve 513, may be coupled more distally than the second body member 520 to a medical device such as a drainage bag or a collection bag. Stated another way, the valve 513 may be disposed on the "patient" side of the break-away connector 500. Furthermore, a first end of a catheter may be coupled to the first body member 512 and a second end of the catheter may be coupled to or disposed within a patient. In such a configuration, the catheter may be configured such that fluid flow from the patient is inhibited, limited, or minimized if the first body member 510 and the second body member 520 of the break-away connector 500 decouple. Other configurations of the break-away connector 500 and the valve 513 are also within the scope of this disclosure. For example, the break-away connector 500 may comprise two valves, a first valve disposed on the drainage bag "side" of the break-away connector 500 and a second valve disposed on the patient "side" of the break-away connector 500. In such a configuration, flow of fluid from each of the patient and the drainage bag may be inhibited, limited, or minimized upon uncoupling of the first body member 510 and the second body member 520 of the break-away connector 500.

FIG. 5C is an exploded cross-sectional side view of the break-away connector 500 of FIG. 5A. As depicted, the first body member 510 can comprise two resilient arms 516a, 516b. Additionally, the slot 518a can be a least partially disposed between each of the two resilient arms 516a, 516b. As discussed above, the second body member 520 can comprise one or more ribs 528a, 528b (see FIGS. 5A and 5B). In certain embodiments, at least a portion of the one or more ribs 528a, 528b can be configured to be disposed within at least a portion of the one or more slots 518a when the first body member 510 is coupled to the second body member 520, such that rotation of the first body member 510 in relation to the second body member 520 around a longitudinal axis of the break-away connector 500 may be substantially limited or minimized. Stated another way, the engagement or interaction of the first body member 510 with the second body member 520, via the slots, resilient arms, and ribs, may substantially limit or minimize displacement or rotation of the first body member 510 and the second body member 520 between each of the first configuration or setting and the second configuration or setting, and vice versa. Still further, interaction of the one or more ribs 528a, 528b (see FIGS. 5A and 5B) and a portion of the one or more slots 518a may facilitate alignment of the first body member 510 and the second body member 520 when coupled.

In some other embodiments, the first body member 510 may comprise only one resilient arm, wherein the one resilient arm may comprise a single slot. Furthermore, the second body member 520 may comprise only one rib, wherein at least a portion of the rib is configured to be disposed within at least a portion of the slot when the first and second body members 510, 520 are coupled to each other, such that rotation of the first body member 510 in relation to the second body member 520 around the longitudinal axis of the break-away connector 500 is substantially limited or minimized. As discussed above, engagement or interaction of the rib with the slot may substantially limit or minimize rotation of the first body member 510 in relation to the second body member 520, or vice versa.

As shown in FIG. 5C, the first body member 510 can further comprise a first lumen 505 disposed within at least a portion of the first body member 510, wherein the first lumen 505 is configured to provide fluid communication between a first end and a second end of the first body member 510. The second body member 520 can further comprise a second lumen 506 disposed within at least a portion of the second body member 520, wherein the second lumen 506 is configured to provide fluid communication between a first end and a second end of the second body member 520. Furthermore, when the first and second body members 510, 520 are coupled to one another, the first lumen 505 may be configured to be in fluid communication with the second lumen 506 (i.e., the first lumen 505 may be substantially aligned with the second lumen 506).

The break-away connector 500, as illustrated, may further comprise the seal member 532, wherein the seal member 532 is configured to substantially limit or minimize fluid communication between each of the first lumen 505 and/or the second lumen 506 with an exterior environment of the break-away connector 500 when the first and second body members 510, 520 are coupled to one another (i.e., when the seal member 532 is coupled to the second body member 520 as in FIG. 5D). For example, the seal member 532 may be configured to limit or minimize leakage of a fluid from within the break-away connector 500 to the exterior environment of the break-away connector 500. In certain embodiments, the seal member 532 may be an O-ring or another suitable sealing mechanism.

FIG. 5D is a cross-sectional side view of the break-away connector 500 of FIG. 5A in the coupled state. With reference to each of FIGS. 5C and 5D, the first body member 510 can comprise the first resilient arm 516a and the second resilient arm 516b. As illustrated, the height or profile of the first ridge portion 517a of the first resilient arm 516a can be greater than the height or profile of the second ridge portion 517b of the second resilient arm 516b. Likewise, the second body member 520 can comprise the first ridge portion 527a and the second ridge portion 527b, wherein the height or profile of the first ridge portion 527a can be greater than the height or profile of the second ridge portion 527b. As described above, the break-away connector 500 may comprise one, two, three, four, five, or more resilient arms, each resilient arm comprising a ridge portion. Additionally, the break-away connector 500 may comprise one, two, three, four, five, or more ridge portions of the second body member 520. Each of the plurality of ridge portions 517, 527 of the first body member 510 and/or the second body member 520, respectively, may have different heights or profiles and/or a combination of heights or profiles such that the break-away connector 500 may comprise a variety of coupling strengths or tightnesses. Accordingly, in certain embodiments, the break-away connector 500 may comprise one, two, three, four, five, or more coupling strength or tightness configurations.

In some embodiments, the first configuration or setting may be a high force configuration or setting. In the first configuration or the high force configuration, the first ridge portion 517a of the first resilient arm 516a may engage or interact with the first ridge portion 527a of the second body member 520 (the configuration or setting shown in FIG. 5D). In such a configuration, two high profile ridge portions (e.g., the first ridge portions 517a, 527a) may engage or interact with each other. In certain embodiments, the second configuration may be a low force configuration. In the second configuration or the low force configuration, the first ridge portion 517a of the first resilient arm 516a may engage or interact with the second ridge portion 527b of the second body member 520. In such a configuration, a high profile ridge portion (e.g., the first ridge portion 517a) may engage or interact with a low profile ridge portion (e.g., the second ridge portion 527b). In certain embodiments, uncoupling of a break-away connector 500 when two high profile ridge portions are engaged with each other may utilize or require a greater force than uncoupling of the break-away connector 500 when a high profile ridge portion is engaged with a low profile ridge portion.

With reference again to FIGS. 5A and 5B, the first resilient arm 516a can comprise a first indicium 530a (e.g., an "H" for high or another suitable indicium), and a portion of the second body member 520 adjacent the first ridge portion 527a can comprise a second indicium 530b (e.g., an elongate arrowhead or another suitable indicium). When the first indicium 530a and the second indicium 530b are substantially aligned (i.e., upon coupling of the first and second body members 510, 520), the break-away connector 500 can be in the high force configuration or setting. Conversely, when the first indicium 530a is substantially aligned with a portion of the second body member 520 opposite of the second indicium 530b, the break-away connector 500 can be in the low force configuration or setting. Again, interaction of the one or more ribs 528a, 528b and a portion of the one or more slots 518a may facilitate alignment of the first body member 510 and the second body member 520 when coupled and when selecting between the high force configuration and the low force configuration.

Referring again to FIG. 5D, the valve 513 can be disposed within at least a portion of the first lumen 505. In some embodiments, the valve 513 may be disposed within at least a portion of the second lumen 506. In some other embodiments, a first valve may be disposed within the first lumen 505 and a second valve may be disposed within the second lumen 506.

As illustrated, the break-away connector 500 may comprise a first valve engagement member 534 disposed within the first lumen 505 and/or coupled to the first body member 510. The break-away connector 500 may also comprise a second valve engagement member 535 disposed within the second lumen 506 and/or coupled to the second body member 520. As illustrated, the first valve engagement member 534 comprises a post-like member configured to engage a center portion of a first surface of the valve 513. In some other embodiments, the first valve engagement member 534 may be substantially conical, substantially semi-spherical, or another suitable shape. In contrast, the second valve engagement member 535, as illustrated, comprises a raised, substantially annular surface configured to engage a portion of a second, or opposite, surface of the valve 513 disposed radially in relation to the center portion of the valve 513. In some embodiments, the second valve engagement member 535 may be substantially square, substantially triangular, or another suitable shape. The engagement or interaction of the first and second valve engagement members 534, 535 with the valve 513 may be configured to open the valve 513 when the first and second body members 510, 520 are coupled to one another. For example, the first and second valve engagement members 534, 535 may be displaced toward each other. The first valve engagement member 534 may be configured to displace at least a portion of the central portion of the valve 513 toward the second valve engagement member 535, and the second valve engagement member 535 may be configured to displace at least a portion of the portion of the valve 513 radially disposed relative to the central portion of the valve 513 toward the first valve engagement member 534. Such displacement of the above-described portions of the valve 513 may result in the transition of the valve 513 from the closed configuration to the open configuration.

Other mechanisms of opening the valve 513 are also within the scope of this disclosure. For example, the break-away connector 500 may include only one valve engagement member (i.e., similar to the first valve engagement member 534). Engagement or interaction of the one such valve engagement member with the valve 513 may result in the transition of the valve 513 from the closed configuration to the open configuration. In certain embodiments, the valve 513 may be formed from a resilient material (e.g., a polymeric material or another suitable material) such that the valve 513 is also configured to transition from the open configuration to the closed configuration upon disengagement of the one or more valve engagement members from the valve 513. With reference to FIG. 5D, the valve 513 can further comprise an aperture 536 (e.g., a slit), wherein the aperture 536 may be configured to transition from a closed configuration to an open configuration upon engagement between the one or more valve engagement members 534, 535 and the valve 513. Furthermore, the aperture 536 may also be configured to transition from the open configuration to the closed configuration or setting upon disengagement of the one or more valve engagement members 534, 535 from the valve 513.

In various embodiments, the coupling end portion 514 of the first body member 510 may be configured to be coupled to a first medical device, and the coupling end portion 524 of the second body member 520 may be configured to be coupled to a second medical device. For example, as discussed above, the break-away connector 500 may be configured for use in medical procedures including, but not limited to, drainage of a volume of a fluid from a patient and intravenous feeding of a patient. The break-away connector 500 may be configured to be coupled to a fluid container such as an IV bag or a drainage bag. The break-away connector 500 may also be configured to be coupled to a catheter, wherein at least a portion of the catheter is disposed in a patient at an access site. The break-away connector 500 may be configured to function or operate as a flow regulator in combination with an IV assembly. In some embodiments, the break-away connector 500 may be configured to adjust a rate of flow or passage of a fluid through the break-away connector 500. For example, the break-away connector 500 may further comprise a twist control mechanism or a needle valve.

In certain embodiments, each of the coupling end portions 514, 524 may comprise a different type of coupling mechanism. For example, the coupling end portion 514 may comprise a male connector and the coupling end portion 524 may comprise a female connector. In another example, the coupling end portion 514 may comprise a threaded coupling mechanism (e.g., a female connector or a male connector) and the coupling end portion 524 may comprise a compression fitting, a snap fitting, or another type of suitable fitting. In various other embodiments, each of the coupling end portions 514, 524 may comprise the same type of coupling mechanism. For example, each of the coupling end portions 514, 524 may comprise a female connector. In another example, each of the coupling end portions 514, 524 may comprise a male connector. In yet another example, each of the coupling end portions 514, 524 may comprise a compression fitting, a snap fitting, or another type of suitable fitting.

Figure 6A:
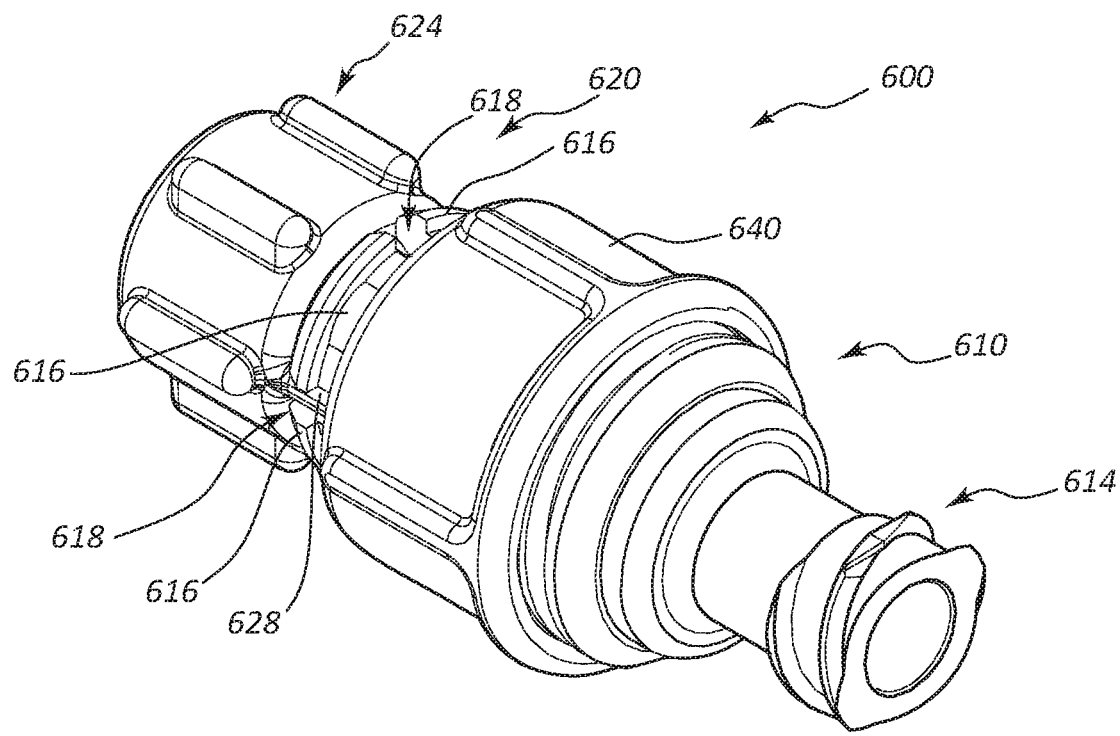
FIG. 6A is a perspective view of another embodiment of a break-away connector in a coupled state.
Figure 6B:
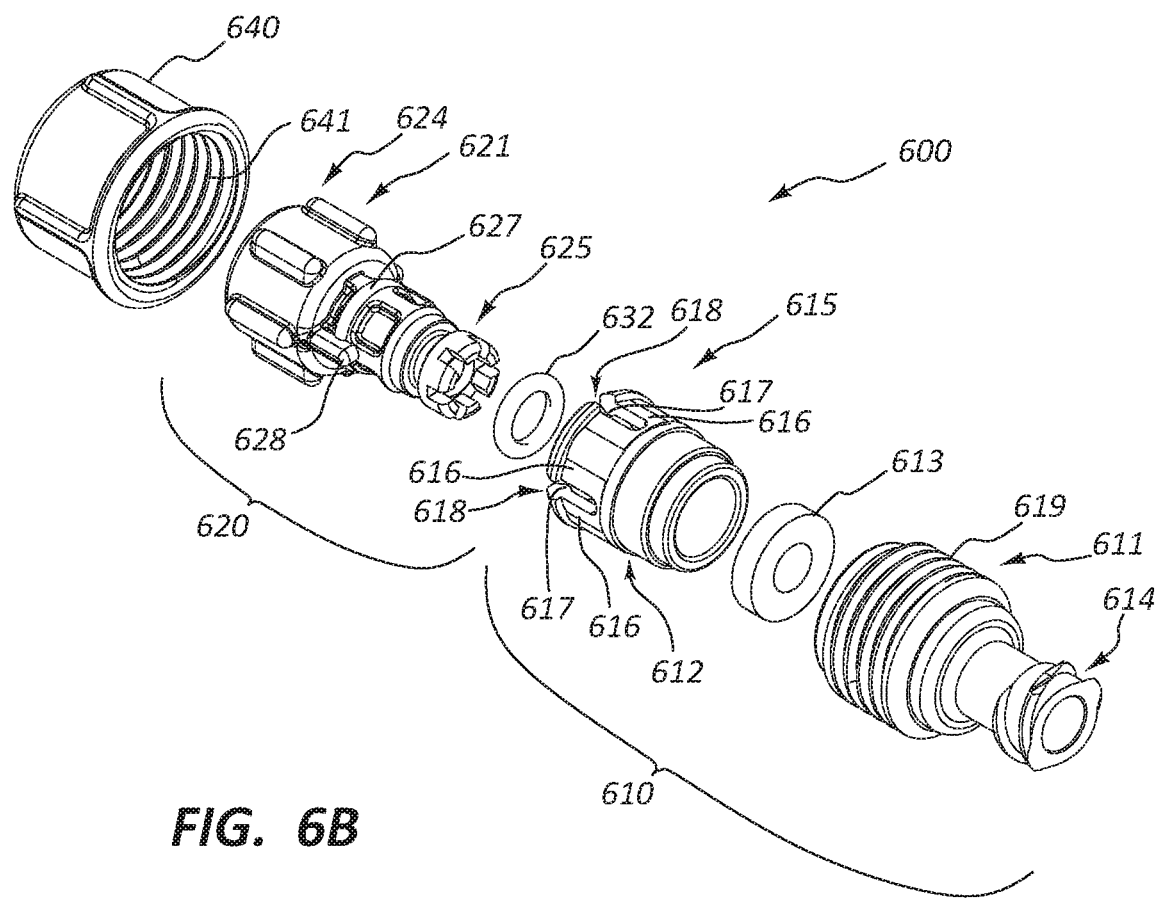
FIG. 6B is an exploded view of the break-away connector of FIG. 6A.

FIG. 6A is a perspective view of a break-away connector 600 in a coupled state, and FIG. 6B is an exploded view of the break-away connector 600 of FIG. 6A. As illustrated, the break-away connector 600 can comprise a first body member 610 and a second body member 620. Analogous to the break-away connectors 100, 200, 300, 400, 500, the first and second body members 610, 620 of the break-away connector 600 are coupleable. Also, the uncoupled state of the break-away connector 600 corresponds to a state wherein the components of each of the first body member 610 and the second body member 620 are assembled but the first body member 610 and the second body member 620 are not coupled. In comparison to the break-away connector 300, for example, the polarity of the valve 613 and the coupling end portions 614, 624 of the break-away connector 600 is switched or inverted.

With reference to FIG. 6B, the first body member 610 may comprise a first portion 611, a second portion 612, and a valve 613. The valve 613 may be disposed within the first body member 610 (i.e., between each of the first portion 611 and the second portion 612). In some embodiments, the valve 613 may be disposed within the second body member 620. In some other embodiments, the break-away connector 600 may comprise more than one valve 613. For example, a first valve may be disposed within the first body member 610 and a second valve may be disposed within the second body member 620. As discussed above regarding the break-away connectors 100, 300, 500, the first portion 611 and the second portion 612 may be coupled to each other by at least one of a compression fit, a snap fit, an adhesive, or another suitable coupling mechanism. The second body member 620 may comprise a first portion 621 and a seal member 632. The seal member 632 may be configured to be coupled to the first portion 621 (see FIGS. 6C and 6D). In some embodiments, the first body member 610 may comprise only a single portion or another suitable number of portions. In certain embodiments, the second body member 620 may comprise two portions or another suitable number of portions.

The first body member 610, as shown, comprises a coupling end portion 614 and a break-away end portion 615. The coupling end portion 614 can be disposed at an end of the first body member 610 opposite from the break-away end portion 615. As illustrated, the coupling end portion 614 comprises a female connector. As stated above, however, other suitable coupling mechanisms are also within the scope of this disclosure. The first body member 610 can further comprise one or more resilient arms 616. For example, the first body member 610 can comprise four resilient arms 616. Furthermore, the one or more resilient arms 616 may comprise one or more ridge portions or raised portions 617. For example, a first resilient arm 616 can comprise a first ridge portion 617, a second resilient arm 616 can comprise a second ridge portion 617, and so on. Additionally, one or more slots 618 may be disposed adjacent, between, or within the one or more resilient arms 616.

The second body member 620 can also comprise a coupling end portion 624 and a break-away end portion 625, wherein the coupling end portion 624 can be disposed at an end of the second body member 620 opposite from the break-away end portion 625. As depicted, the coupling end portion 624 comprises a male connector. Again, as stated above, other suitable coupling mechanisms are also within the scope of this disclosure. The break-away end portion 625 of the second body member 620 can comprise one or more ridge portions or raised portions 627. For example, the break-away end portion 625 of the second body member 620 can comprise two ridge portions 627 disposed around at least a portion of the circumference of the break-away end portion 625. Furthermore, one or more ribs 628 can be disposed adjacent or between the one or more ridge portions 627. In certain embodiments, the one or more ribs 628 may be configured to be at least partially disposed within at least a portion of the one or more slots 618 upon coupling of the first and second body members 610, 620.

In various embodiments, the one or more ridge portions 617 of the first body member 610 may be configured to engage or interact with the one or more ridge portions 627 of the second body member 620 (i.e., upon coupling of the first and second body members 610, 620).

The break-away connector 600, as shown, can further comprise a collar member 640. As illustrated in FIG. 6B, the collar member 640 can include a plurality of threads 641, wherein the threads 641 are disposed on an interior surface of the collar member 640. Furthermore, the collar member 640 can be disposable around at least a portion of the first body member 610, wherein the plurality of collar member threads 641 may be configured to engage or interact with a plurality of threads 619 disposed on an exterior surface of the first portion 611 of the first body member 610. In some embodiments, the threads 619 may be disposed on a different portion of the first body member 610 (e.g., the second portion 612). In some other embodiments, a first portion of the threads 619 may be disposed on the first portion 611 and a second portion of the threads 619 may be disposed on the second portion 612. In yet some other embodiments, the threads 619, or at least a portion of the threads 619, may be disposed on the second body member 620 and the collar member 640 may be disposable around at least a portion of the second body member 620.

In certain embodiments, the collar member 640 may further comprise a first portion of a ratchet assembly (not shown). Furthermore, a second portion of the ratchet assembly may be disposed on at least a portion of the first body member 610 and/or the second body member 620. In some embodiments, a plurality of teeth of the first portion of the ratchet assembly may engage or interact with a plurality of detents of the second portion of the ratchet assembly, or vice versa. The ratchet assembly may aid in the continuous or incremental adjustment or tuning of the collar member 640, as discussed above in reference to the collar member 340. For example, rotation of the collar member 640 comprising a first or second portion of the ratchet assembly may generate one or more "clicks" that may be felt and/or heard by the user. Thus, the user may be able to adjust a degree or level of coupling strength of the break-away connector 600 according to rotating the collar member 640 through a desired or predetermined number of "clicks."

In some embodiments, the ratchet assembly may limit or minimize accidental or unintentional rotation of the collar member 640. The ratchet assembly may also limit or minimize rotation of the collar member 640 in at least one direction. For example, a practitioner may desire that the strength or tightness configuration in which the break-away connector 600 is disposed does not or cannot substantially adjust or change without input from the practitioner. Stated another way, in some embodiments, the break-away connector 600 may be configured (e.g., with a ratchet assembly) such that the collar member 640 and/or the break-away connector 600 do not self-adjust or such that self-adjustment is substantially inhibited, limited, or minimized.

Figure 6C:
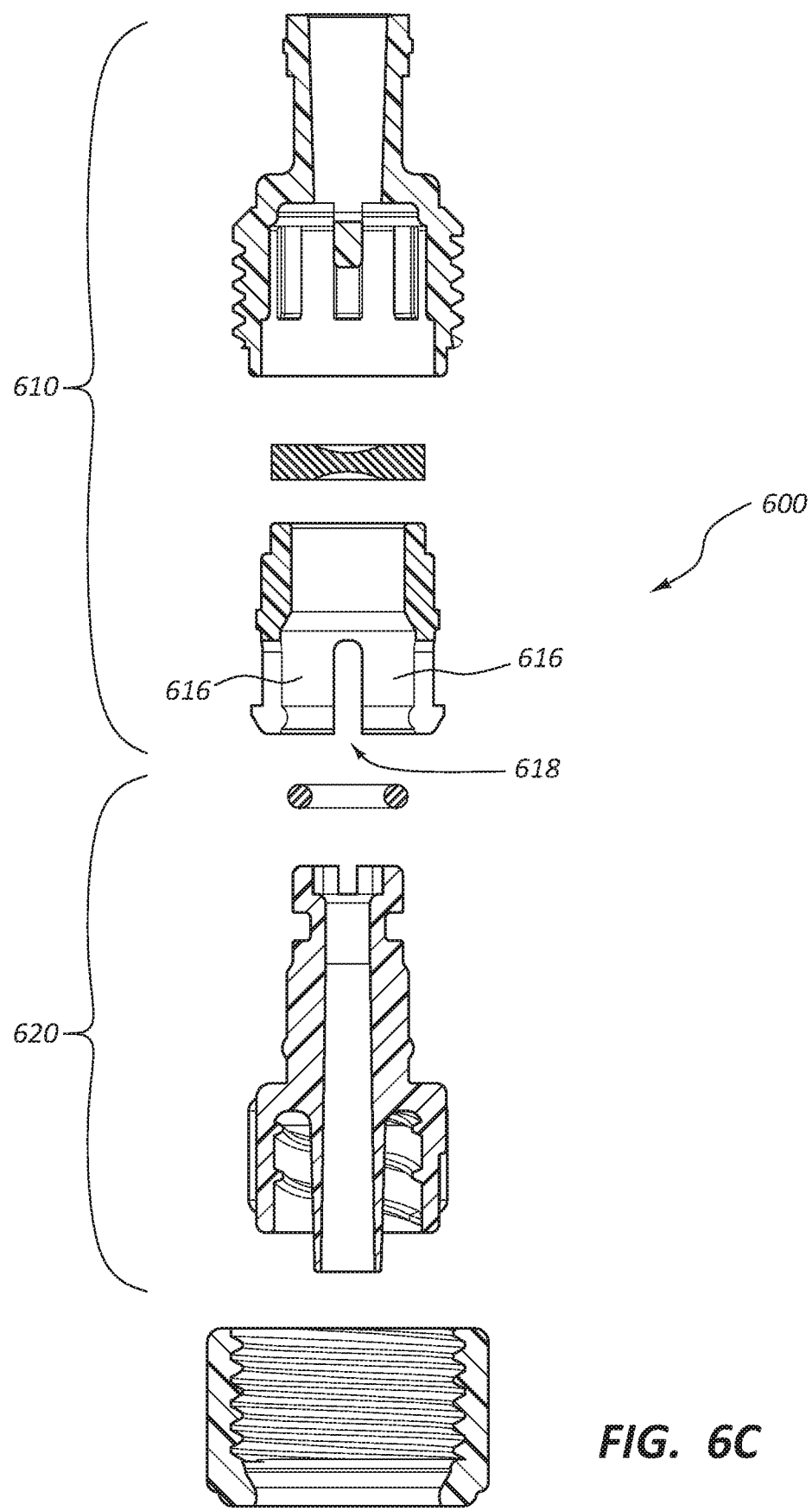
FIG. 6C is an exploded cross-sectional side view of the break-away connector of FIG. 6A.

FIG. 6C is an exploded cross-sectional side view of the break-away connector 600 of FIG. 6A. The first body member 610 comprises a plurality of resilient arms 616. As stated above, in some other embodiments, the first body member 610 may comprise one, two, three, four, five, six, or more resilient arms. A slot 618 can be at least partially disposed between each of the resilient arms 616. As discussed above, the second body member 620 can comprise one or more ribs 628 (see FIGS. 6A and 6B). In some embodiments, at least a portion of at least one of the ribs 628 can be configured to be disposed within at least a portion of the slots 618 upon coupling of the first and second body members 610, 620. The disposition of at least a portion of the rib 628 within at least a portion of at least one slot 618 may be configured to substantially limit or minimize rotation of the first body member 610 in relation to the second body member 620 around a longitudinal axis of the break-away connector 600 when the first and second body members 610, 620 are coupled to one another.

Figure 6D:
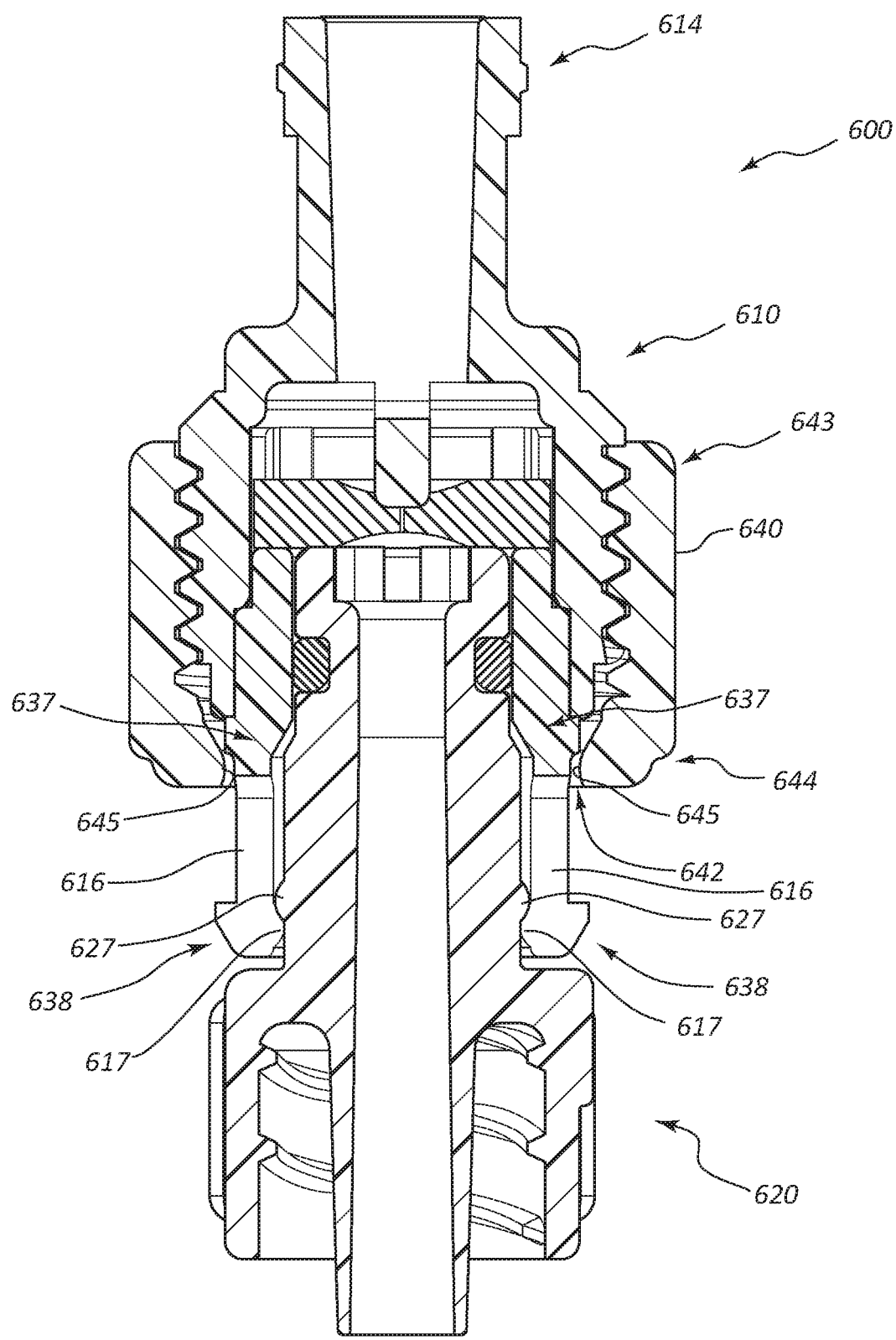
FIG. 6D is a cross-sectional side view of the break-away connector of FIG. 6A in the coupled state.

FIG. 6D is a cross-sectional side view of the break-away connector 600 of FIG. 6A, in the coupled state. With reference to each of FIGS. 6C and 6D, the first body member 610 can comprise a plurality of resilient arms 616, wherein each resilient arm 616 comprises a ridge portion 617. Likewise, the second body member 620 can comprise a plurality of ridge portions 627. As described above, the break-away connector 600 may comprise one, two, three, four, five, or more resilient arms, each resilient arm comprising a ridge portion. Additionally, the break-away connector 600 may comprise one, two, three, four, five, or more ridge portions 627 of the second body member 620. Each of the plurality of ridge portions 617, 627 of the first body member 610 and/or the second body member 620, respectively, may have different heights or profiles and/or a combination of heights or profiles such that the break-away connector 600 may comprise a variety of coupling strengths or tightnesses. Accordingly, in certain embodiments, the break-away connector 600 may comprise one, two, three, four, five, or more coupling strength or tightness configurations.

With continued reference to FIG. 6D, the collar member 640 may be configured to limit or minimize radial movement of the one or more resilient arms 616 outward relative to the longitudinal axis of the break-away connector 600. For example, as the collar member 640 is threadably rotated around at least a portion of the first body member 610, the collar member 640 can be displaced toward the coupling end portion 614 of the first body member 610 and consequently a lesser portion of the collar member 640 may be disposed at or adjacent the one or more resilient arms 616. As depicted, the collar member 640 comprises a first end portion 643 and a second end portion 644. The collar member 640 further comprises a lumen 642 disposed within the collar member 640 between at least the first end portion 643 and the second end portion 644. The diameter of the lumen 642 of the collar member 640 adjacent the first end portion 643, as shown, is greater than the diameter of the lumen 642 adjacent the second end portion 644. The interior surface of the collar member 640 adjacent the second end portion 644 can form a resilient arm engagement surface 645. When the resilient arm engagement surface 645 is disposed at or adjacent a base portion 637 of each of the resilient arms 616 (i.e., in a second position), as depicted in FIG. 6D, the length of the portion of each of the resilient arms 616 that is not disposed adjacent the interior surface of the collar member 640 is greater than when the collar member 640 is disposed at or adjacent an end portion 638 of each of the resilient arms 616 (i.e., in a first position). Stated another way, displacement of the collar member 640 longitudinally with respect to the resilient arms 616 may increase or decrease the effective length of the resilient arms 616.

The effective length of the resilient arms 616 may correlate to the force needed to couple or decouple the first body member 610 and the second body member 620. Interaction of the ridge portions 617 on the resilient arms 616 and the ridge portions 627 on the second body member 620 during coupling or uncoupling tend to displace the resilient arms 616 radially outward. The longer the effective length of the resilient arms 616, the relatively less force required to displace the ridge portions 617 of the resilient arms 616 radially outward. Shortening the effective length of the resilient arms 616 increases the necessary force. Thus displacement of the collar 640 may allow for adjustment of the coupling or uncoupling force associated with the break-away connector 600, even in embodiments where the ridge portions 617 have a uniform height around the circumference of the first body member 610 and the ridge portions 627 of the second body member 620 have a uniform height around the circumference of the second body member 620.

In the configuration as depicted in FIG. 6D (e.g., the second configuration or the second setting), wherein the resilient arm engagement surface 645 is disposed at or adjacent the base portion 637 of each of the resilient arms 616, each of the resilient arms 616 is less restricted and more freely able to be biased or to extend radially outward relative to the longitudinal axis of the break-away connector 600 such that each of the ridge portions 617 of the first body member 610 can be easily, or more easily, disengaged or uncoupled from the ridge portions 627 of the second body member 620. In contrast, when the resilient arm engagement surface 645 is disposed at or adjacent the end portion 638 of each of the resilient arms 616 (e.g., in the first configuration or the first setting), each of the resilient arms 616 is more restricted and less freely able to be biased or to extend radially outward relative to the longitudinal axis of the break-away connector 600, such that the ridge portions 617 of the first resilient arms 616 can be less easily disengaged or uncoupled from the ridge portions 627 of the second body member 620. Stated another way, it may be more difficult to disengage or uncouple the ridge portions 617 from the ridge portions 627 when the collar member 640 is in the first position compared to when the collar member 640 is in the second position.

In some embodiments, the collar member 640 may be continuously or incrementally adjustable between each of the first position and the second position such that the strength of the coupling of the first and second body members 610, 620, or a degree or level of coupling strength between the first and second body members 610, 620, is continuously or incrementally adjustable or tunable. In some embodiments, when the collar member 640 is in the first position the break-away connector 600 can be in the first configuration and when the collar member 640 is in the second position the break-away connector 600 can be in the second configuration. The first configuration, as described above, may be a high force configuration and the second configuration, as described above, may be a low force configuration. For example, a practitioner uncoupling the first and second body members 610, 620 may apply, exert, or utilize a greater amount of force (i.e., mechanical force) to uncouple the first and second body members 610, 620 when the break-away connector 600 is in the first configuration in comparison to when the break-away connector 600 is in the second configuration.

Methods related to use of break-away connectors, are also disclosed herein. In some embodiments, a method of coupling a break-away connector may comprise grasping each of a first body member and a second body member. The method may further comprise determining a desired level of coupling strength and coupling the first body member to the second body member in a first configuration or in a first setting if a high or higher level of coupling strength is desired and coupling the first body member to the second body member in a second configuration or in a second setting if a low or lower level of coupling strength is desired.

In some embodiments, the method of coupling the break-away connector may further comprise rotating a collar member around a portion of the first body member such that the level of coupling strength continuously or incrementally decreases between the first configuration and the second configuration, or rotating the collar member around a portion of the first body member such that the level of coupling strength continuously or incrementally increases between the second configuration and the first configuration. In certain embodiments, the method may comprise engaging a low profile ridge of the first body member with a high profile ridge of the second body member to couple the first body member to the second body member in the first configuration. In certain other embodiments, the method may comprise engaging a high profile ridge of the first body member with a high profile ridge of the second body member to couple the first body member to the second body member in the second configuration. As can be appreciated, additional methods and/or method steps can be derived from FIGS. 1A-6D and the corresponding disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially aligned" is recited with respect to a feature, it is understood that in further embodiments, the feature can have a precisely aligned configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A break-away connector, comprising: a first body member having a coupling end portion and a break-away end portion; a second body member having a coupling end portion and a break-away end portion, wherein the break-away end portion of first body member is configured to engage the break-away end portion of the second body member upon coupling of the first body member to the second body member; and a collar coupled to the first body member, the collar longitudinally displaceable with respect to the first body member, wherein the break-away connector is selectively configurable between a coupled state having the first body member coupled to the second body member and an uncoupled state having the first body member uncoupled from the second body member, the collar remaining coupled to the first body member in both the coupled state and decoupled state, wherein a first force required to uncouple the first body member from the second body member when the collar is in a first position is greater than a second force required to uncouple the first body member from the second body member when collar is in a second position; wherein the first body member comprises two or more resilient arms and a slot is disposed between two of the resilient arms, wherein the second body member comprises a rib, and wherein a portion of the rib is configured to be disposed within a portion of the slot when the first body member is coupled to the second body member, such that rotation of the first body member in relation to the second body member around a longitudinal axis of the break-away connector is limited.

2. The break-away connector of claim 1, wherein the break-away end portion of the first body member comprises one or more resilient arms, each resilient arm having one or more ridge portions, wherein the break-away end portion of the second body member comprises one or more ridge portions, and wherein the one or more ridge portions of the first body member are configured to engage the one or more ridge portions of the second body member upon the coupling of the first body member to the second body member.

3. The break-away connector of claim 2, wherein a portion of the collar is configured to limit radial movement of the one or more resilient arms radially outward relative to a longitudinal axis of the break-away connector.

4. The break-away connector of claim 1, further comprising a valve disposed within at least one of a lumen of the first body member or a lumen of the second body member.

5. The break-away connector of claim 4, wherein the valve is configured to open upon coupling of the first body member to the second body member.

6. The break-away connector of claim 4, further comprising a valve engagement member disposed within at least one of the lumen of the first body member and the lumen of the second body member,
wherein the valve engagement member is configured to open the valve upon coupling of the first body member to the second body member.

7. The break-away connector of claim 1, wherein the first body member comprises a slot and the second body member comprises a rib, and
wherein a portion of the rib is configured to be disposed within a portion of the slot when the first body member is coupled to the second body member, such that rotation of the first body member in relation to the second body member around a longitudinal axis of the break-away connector is limited.

8. The break-away connector of claim 1, wherein the collar is selectively adjustable between the first position and the second position, and a force required to uncouple the first body member from the second body member is variable between the first force and the second force as the collar is adjusted between the first position and the second position.

9. The break-away connector of claim 1, wherein the collar is threadably coupled to the first body member.

10. The break-away connector of claim 9, wherein rotation of the collar is configured to incrementally adjust a level of coupling strength between the first body member and the second body member.

11. The break-away connector of claim 10, wherein rotation of the collar adjusts a deflectable length of at least one of the two or more resilient arms.

* * * * *